(12) United States Patent
Oh et al.

(10) Patent No.: US 8,414,924 B2
(45) Date of Patent: Apr. 9, 2013

(54) PREPARATION FOR TREATING HEART DISEASE USED IN CELL THERAPY

(75) Inventors: Hidemasa Oh, Kyoto (JP); Naofumi Takehara, Kyoto (JP); Hiroaki Matsubara, Kyoto (JP); Yasuhiko Tabata, Kyoto (JP)

(73) Assignee: Kyoto University, Kyoto-shi, Kyoto (JP)

( * ) Notice: Subject to any disclaimer, the term of this patent is extended or adjusted under 35 U.S.C. 154(b) by 0 days.

(21) Appl. No.: 12/681,940

(22) PCT Filed: Oct. 9, 2008

(86) PCT No.: PCT/JP2008/068809
§ 371 (c)(1),
(2), (4) Date: Jul. 12, 2010

(87) PCT Pub. No.: WO2009/048166
PCT Pub. Date: Apr. 16, 2009

(65) Prior Publication Data
US 2010/0303909 A1    Dec. 2, 2010

(30) Foreign Application Priority Data
Oct. 10, 2007    (JP) .................................. 2007-265008

(51) Int. Cl.
*A61K 35/34* (2006.01)
*A61K 9/00* (2006.01)
*A61P 9/00* (2006.01)

(52) U.S. Cl. ...................................... 424/484; 424/93.7

(58) Field of Classification Search .......................... None
See application file for complete search history.

(56) References Cited

U.S. PATENT DOCUMENTS
6,902,522 B1 *    6/2005    Walsh et al. .................... 600/37

FOREIGN PATENT DOCUMENTS

| EP | 1857544 A1 | 11/2007 |
|----|------------|---------|
| JP | H05-111382 A | 5/1993 |
| JP | 2001-316282 A | 11/2001 |
| JP | 2002-145797 A | 5/2002 |
| JP | 2004-167202 A | 6/2004 |
| WO | WO2006/093276 A1 | 9/2006 |

OTHER PUBLICATIONS

Hoshino et al. (Gene Therapy. 2006; 13: 1320-1327).*
Shimizu (Japanese Society for Biomaterials. 2003; 21(3): 194-195, pp. 1-18).*
Tateishi et al. (Biochemical and Biophysical Research Communications. published online Nov. 27, 2006; 352: 635-641).*
Beltrami et al. (Cell. 2003; 114:763-776).*
Ferreira-Martins et al. (Circulation Research. 2012; 110: 701-715).*
Hiroaki Matsubara,Hito Shinkin Kokkakaukin Karano Shinkin Kansaibokaku no Juritsu to Makki Shinfuzen eno Kansaibo Ishoku Iryo Jitsugenka e Mukete no Kenkyo Kiban Keisei, Reseach of New Medical Devices, Mar. 25, 2007, vol. 12, pp. 100-101(with translation).
Hidemasa Oh, Hito Shinzonai Kansaibo o Mochiita Jika Saibo Ishoku ni yoru Shinkin Saisei Iryo, Regenerative Medicine, Feb. 22, 2008, vol. 7, suppl., p. 160 (with translation).
Schuppan D. et al., Collagens in the Liver Extracellular Matrix Bind Hepatocyte Growth Factor, Gastroenterology, vol. 114, pp. 139-152 (1998).
Nakamura et al., Molecular cloning and expression of human hepatocyte growth factor, Nature, vol. 343, pp. 440-443 (Nov. 23, 1989).
Miyazawa et al., Molecular cloning and sequence analysis of cDNA for human hepatocyte growth factor, Biochem. Biophys. Res. Commun., 163, pp. 967-973 (1989).
Beltrami, A., et al., "Adult cardiac stem cells are multipotent and support myocardial regeneration", Cell, vol. 114, pp. 763-776 (Sep. 19, 2003).

* cited by examiner

*Primary Examiner* — Scott Long
(74) *Attorney, Agent, or Firm* — Fitch, Even, Tabin & Flannery, LLP

(57) ABSTRACT

An object of the present invention is to establish a cell transplantation method which can markedly improve the survival of grafted pluripotent stem cells and the efficiency of cardiomyocyte regeneration in cell therapy using pluripotent stem cells derived from heart tissue and can treat heart disease further effectively. Specifically, according to the present invention, enhancement in the survival of grafted pluripotent stem cells and significant improvement in the efficiency of cardiomyocyte regeneration are achieved by using, in combination, pluripotent stem cells derived from heart tissue and a hydrogel containing a basic fibroblast growth factor (bFGF) in cell therapy for heart disease.

19 Claims, 11 Drawing Sheets

PREPARATION FOR TREATING HEART DISEASE USED IN CELL THERAPY

CROSS-REFERENCE TO RELATED APPLICATIONS

This application is a U.S. National Phase entry of International Application No. PCT/JP2008/068809, filed on Oct. 9, 2008, which claims priority to Japanese Application No. 2007-265008, filed on Oct. 10, 2007. The complete disclosures of the referenced applications, including any sequence listing(s), are incorporated herein by reference.

TECHNICAL FIELD

The present invention relates to a preparation for treating heart disease used in cell therapy. More specifically, the present invention relates to a preparation for treating heart disease which is markedly excellent in the survival of graft cells and cardiomyocyte regeneration in the treatment of heart disease using cell therapy and can treat the heart disease further effectively.

BACKGROUND ART

In regenerative medicine, medical technology has been studied actively in recent years to repair and regenerate target tissue and organ by transplanting stem cells. Stem cells capable of differentiating into mature cells of various tissues or organs have been found so far and studied for their clinical application to cell transplantation.

For example, bone marrow-derived cells or skeletal myoblasts have been found to be capable of differentiating into cardiomyocytes. It has been reported that using these cells, cardiomyocytes regeneration is observed in a short time by cell transplantation to heart tissue. However, such cardiomyocyte regeneration observed by the transplantation of the bone marrow-derived cells or skeletal myoblasts has been shown to be attributed not to cardiomyocytes substantially regenerated by the transplanted cells but to cytokine secretion for myocardial protection induced by paracrine effect.

Moreover, the present inventors have developed a technique of separating and purifying, from heart tissue, pluripotent stem cells having the ability to differentiate into various mature cells including cardiomyocytes (the pamphlet of International Publication No. WO 2006/093276). Such pluripotent stem cells derived from heart tissue have been shown to have the excellent ability to differentiate into cardiomyocytes and be most useful, among previously reported cardiac stem cells, in the treatment of heart disease using cell transplantation.

Nevertheless, however useful donor stem cells used in cell transplantation, these donor stem cells (transplanted cells) mostly die 2 weeks after their single transplantation and are thus grafted insufficiently. As a result, it has been shown that the donor stem cells cannot exert the desired therapeutic effect to a maximum extent. Thus, improvement in the survival of grafted donor stem cells in the recipient host environment has been thought to be important for enhancing the therapeutic effect of cell transplantation.

On the other hand, it has previously been reported that a hydrogel containing a growth factor can improve the survival ratio of grafted donor cells in cell therapy by controlled-release of the growth factor in the cell transplantation site (Japanese Patent Laid-Open No. 2002-145797). However, no reports have been made so far about cell transplantation using, in combination, pluripotent stem cells derived from heart tissue and a hydrogel containing a growth factor.

DISCLOSURE OF THE INVENTION

Problems to be Solved by the Invention

Moreover, the present inventors have confirmed by studies that merely the combined use of pluripotent stem cells derived from heart tissue and a hydrogel in transplantation to heart tissue may be insufficient for the survival of the graft in the host heart tissue or the efficiency of cardiomyocyte regeneration, as shown in experimental data described later. Specifically, even if the most clinically useful pluripotent stem cells derived from heart tissue among previously reported myocardial stem cells are used in conventional techniques, a cell transplantation method cannot be established under the present circumstances, which is capable of effectively improving the survival of the graft in the host heart tissue and making the most of the therapeutic effect of the pluripotent stem cells.

Thus, an object of the present invention is to establish a cell transplantation method which can markedly improve the survival of grafted pluripotent stem cells and the efficiency of cardiomyocyte regeneration in cell therapy using pluripotent stem cells derived from heart tissue and can treat heart disease further effectively.

Means for Solving the Problems

To attain the object, the present inventors have studied various cell transplantation conditions and have found, after much trial and error, that enhancement in the survival of grafted pluripotent stem cells and significant improvement in the efficiency of cardiomyocyte regeneration are achieved by using, in combination, pluripotent stem cells derived from heart tissue and a hydrogel containing a basic fibroblast growth factor (bFGF). The present inventors have further found that the survival of grafted pluripotent stem cells and cardiomyocyte regeneration can be further improved by setting the dose of the pluripotent stem cells to $10 \times 10^5$ cells or less per kg body weight of a patient. Based on these findings, the present invention has been completed.

Specifically, the present invention provides a preparation for treating heart disease used in cell therapy shown below.

The present invention provides a preparation for treating heart disease used in cell therapy, comprising: a hydrogel containing bFGF; and pluripotent stem cells derived from heart tissue. In this context, the preparation for treating heart disease may be formulated as a kit comprising the hydrogel and the pluripotent stem cells.

Examples of the hydrogel used in the preparation for treating heart disease of the present invention can include gelatin, collagen, starch, pectin, hyaluronic acid, chitin, chitosan, and alginic acid, and derivatives of these materials. Among them, a collagen or gelatin hydrogel is preferable.

It is preferred that the preparation for treating heart disease of the present invention should be formulated such that the dose of the hydrogel containing bFGF is 1 to 100 μg per kg body weight of a patient in terms of the amount of the bFGF.

It is preferred that the hydrogel should be in a sheet form.

The preparation for treating heart disease of the present invention may further comprise a non-biodegradable polymer support. The hydrogel in a sheet form is immobilized on this polymer support and administered to an epicardium.

Examples of the non-biodegradable polymer support can include polytetrafluoroethylene (Gore-Tex (registered trademark)).

It is preferred that the preparation for treating heart disease of the present invention should be formulated such that the bFGF is administered in an amount of at least 1 to 100 µg with respect to the amount of the pluripotent stem cells of $5\times10^6$ cells per kg body weight.

It is preferred that the preparation for treating heart disease of the present invention should be formulated such that the pluripotent stem cells derived from heart tissue are administered in an amount of $1\times10^6$ cells or less per kg body weight of a patient, more preferably in an amount of $1\times10^5$ to $10\times10^5$ cells per kg body weight of a patient.

It is preferred that the pluripotent stem cells derived from heart tissue used in the present invention should be CD90-positive, CD29-positive, CD73-positive, stro-1-positive, and CD105-positive. Such pluripotent stem cells are prepared, for example, through the following steps:
(i) enzymatically treating a heart tissue slice collected from a mammal to prepare a cell suspension;
(ii) separating a heart tissue-derived cell group from the cell suspension by a density gradient method; and
(iii) suspension-culturing the obtained heart tissue-derived cell group in a medium containing bFGF and an epidermal growth factor and then selecting and separating cells forming a floating sphere.

The pluripotent stem cells derived from heart tissue used in the present invention may be derived from the heart tissue of a patient (autotransplantation) or may be derived from heart tissue other than that of a patient (allotransplantation). Alternatively, the pluripotent stem cells may be an established cell line.

Advantages of the Invention

A preparation for treating heart disease of the present invention can markedly improve the survival of grafted pluripotent stem cells derived from heart tissue in the treatment of heart disease using cell therapy and can regenerate cardiomyocytes. Using the preparation for treating heart disease of the present invention, cell therapy for heart disease conducted on, for example, severe heart failure patients in need of heart transplantation can achieve the sufficient degree of amelioration necessary for living without the aid of transplanted artificial heart, and furthermore, continuous drug therapy can be expected to offer such a degree of amelioration that the need of heart transplantation is eliminated over the long term. Thus, using the preparation for treating heart disease of the present invention, cell therapy for heart disease can achieve the degree of amelioration of the disease unfeasible by conventional cell therapy.

Thus, the preparation for treating heart disease of the present invention is expected to be clinically applied as an innovative lifesaving method for patients in need of heart transplantation, terminal heart failure patients having the difficulty in living without the aid of artificial heart, or patients equivalent thereto, which are an estimated 7,000 to 10,000 people in Japan.

Moreover, pluripotent stem cells derived from heart tissue exhibit the features of mesenchymal stem cells and are therefore said to hardly cause immune rejection. Therefore, the preparation for treating heart disease of the present invention is clinically practicable not only to autologous cell transplantation but also to allogeneic cell therapy. Hence, the preparation for treating heart disease of the present invention can effectively treat heart disease in the aged presumably with the small abundance of pluripotent stem cells in their hearts, by adopting an established pluripotent stem cell line derived from human heart tissue and using this established cell line for allogeneic cell therapy.

In actuality, even cells having pluripotency do not always have the high degree of differentiation into cardiomyocytes. Thus, the clinical trials of cell therapy in the heart have failed using bone marrow stem cells or skeletal myoblasts. The present invention has succeeded in in-vivo cell therapy for the first time by using pluripotent stem cells derived from heart tissue and bFGF in combination. This is surely excellent effect unexpected from conventional techniques.

BRIEF DESCRIPTION OF THE DRAWINGS

FIG. 1A shows spheres observed after 1 day of culture, and FIG. 1B shows spheres observed after 7 days of culture;

FIG. 16A) or infarction size (infarct volume; FIG. 16B) in a bFGF+human CDC-cotransplanted group (bFGF+CDC) and an untreated group (control)

Figure 1:
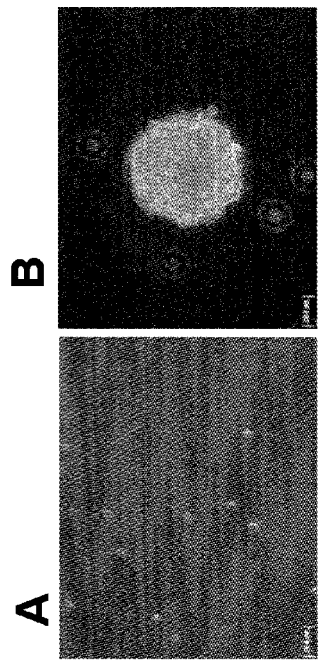
FIG. 1 is a photograph showing floating spheres (cell masses) formed after suspension culture of a human heart tissue-derived cell group separated by Percoll density gradient centrifugation.

The present specification encompasses the contents described in the specification of Japanese Patent Application No. 2007-265008 (issued on Oct. 10, 2007) that serves as a basis for the priority of the present application.

BEST MODE FOR CARRYING OUT THE INVENTION

A preparation for treating heart disease of the present invention is used in cell therapy for heart disease and characterized by comprising, in combination: a hydrogel containing bFGF; and pluripotent stem cells derived from heart tissue. Hereinafter, each component of the preparation for treating heart disease of the present invention will be described in detail.

Hydrogel Containing bFGF

The hydrogel containing bFGF is not particularly limited as long as it is a biodegradable polymer hydrogel. For example, hydrogels of gelatin, collagen, starch, pectin, hyaluronic acid, chitin, chitosan, and alginic acid, and derivatives thereof can be used alone or in combination. The hydrogel containing bFGF can be prepared by dipping the biodegradable polymer in a bFGF-containing aqueous solution for swelling or by adding dropwise an appropriate amount of a bFGF-containing solution to the biodegradable polymer swollen in a buffer.

Preferable examples of the hydrogel can include collagen and gelatin hydrogels. Collagen is a main biological protein that accounts for ⅓ of proteins that make up living organisms, and originally interacts in itself with various biologically active peptides. For example, it has been reported that certain cell growth factors interact with collagen via intermolecular force (e.g., Schuppan, D. et al., Gastroenterology., vol. 114, p. 139, 1998). This interaction can include various interactions such as electrostatic, hydrophobic, and hydrogen-bonding interactions and differs in strength and rate depending on combinations of biologically active peptides with collagen. Through these interactions, bFGF and collagen serving as a carrier physically bind to each other and form a stable bFGF-containing collagen hydrogel.

Atelocollagen free from antigenicity is preferably used as the collagen. The collagen may be a commercially available collagen sponge or may be prepared by methods known in the art. It is also preferred that the collagen should be low soluble in water. Collagen, which is also soluble in water, makes the bFGF-containing collagen hydrogel water-soluble, depending on solubilization methods (including acid treatment, alkali treatment, and enzymatic treatment). This water-soluble bFGF-containing collagen hydrogel, when administered in vivo, transiently releases the bFGF therefrom and hardly achieves stable slow release. Such water-insoluble collagen can be obtained as a collagen hydrogel with a water content of 85 to 99% according to, for example, Japanese Patent Laid-Open No. 2001-316282, by subjecting collagen to cross-linking treatment.

Any collagen may be used, irrespective of the species, tissue site, and age of an animal serving as a starting material thereof. Moreover, the collagen used is also independent of its extraction and purification methods. Although there exist dozen types of collagens, any type of collagen or collagen mixtures that can be made water-insoluble by cross-linking treatment can be applied as the collagen used in the present invention. The collagen is preferably, for example, type I, III, or IV collagen.

The collagen cross-linking can be performed according to conventional methods known in the art. Specific examples of the methods include a method using a chemical cross-linking agent and a cross-linking method using heat treatment or UV irradiation. For example, an aqueous collagen solution (preferably, approximately 0.3 wt % solution) is whipped using a homogenizer, then frozen, and lyophilized to prepare a collagen sponge. Subsequently, this uncrosslinked collagen sponge is cross-linked by chemical cross-linking agent, heat, or UV treatment. For the chemical cross-linking, a preferable cross-linking agent is appropriately selected depending on the type of the collagen used. Usually, cross-linking agents are used such as formalin, glutaraldehyde; e.g., 1-ethyl-3-(3-dimethylaminopropyl)carbodiimide hydrochloride and 1-cyclohexyl-3-(2-morpholimoethyl)carbodiimide-metho-p-toluenesulfonate], epichlorohydrin, and diepoxy compounds [e.g., bisepoxydiethylene glycol and 1,4-bis-(2,3-epoxypropoxy-butane)]. The cross-linking agent solution is contacted at a cross-linking agent concentration of $10^{-3}$ to 10 wt %, preferably $10^{-2}$ to 1 wt %, with the uncrosslinked collagen sponge at 4 to 40° C., preferably 25 to 30° C., for 3 to 48 hours, preferably 12 to 24 hours.

For the heat cross-linking, the uncrosslinked collagen is left in an atmosphere under reduced pressure (preferably, approximately 10 mmHg) at 110 to 160° C., preferably 120 to 150° C., usually for 1 to 48 hours, preferably 6 to 24 hours. Moreover, for the UV cross-linking, the uncrosslinked collagen is left usually at room temperature, preferably 0 to 40° C., for 6 to 48 hours under a germicidal lamp.

The gelatin hydrogel refers to a hydrogel obtained by cross-linking gelatin. The gelatin used in the present invention can be obtained by various denaturation treatments (e.g., alkali hydrolysis, acid hydrolysis, and enzymatic degradation) from collagen that can be collected from every site in the bodies (e.g. skin, bone, and tendon) of various animal species including cow, pigs, and fishes, or from substances used as collagen. Alternatively, gelatin obtained by denaturing genetically recombinant collagen may be used. The property of gelatin differs depending on materials and treatment methods used. In the present invention, gelatin having any property can be used as a material for the gelatin hydrogel.

Examples of scales indicating the gelatin property include isoelectric point, molecular weight, and zeta potential. The zeta potential is a scale that indicates the degree of electrostatic charge of a substance (gelatin). In the present invention, preferable examples of the gelatin include gelatins which are (i) acidic gelatins obtained by alkali hydrolysis treatment from collagen, (ii) have a molecular weight of approximately 100,000 to approximately 200,000 daltons under non-reducing conditions of SDS-PAGE, and (iii) have a zeta potential of approximately −15 to approximately −20 mV in aqueous solutions. Moreover, acidic gelatin prepared by alkali treatment of bovine bone-derived type I collagen can be used preferably. The acidic gelatin can also be obtained as a sample isoelectric point (IEP) 5.0 from Nitta Gelatin Inc. In this context, basic gelatin prepared by acid treatment can also be obtained as a sample IEP9.0 from Nitta Gelatin Inc. and however, differs greatly in zeta potential from the acidic gelatin as follows:

Acidic gelatin (Nitta Gelatin Inc., sample IEP5.0): approximately −15 to approximately −20 mV, and
Basic gelatin (Nitta Gelatin Inc., sample IEP9.0): approximately +12 to approximately +15 mV.

For the gelatin cross-linking, methods known in the art can be used. Examples of gelatin cross-linking agents include: glutaraldehyde; water-soluble carbodiimide such as 1-ethyl-3-(3-dimethylaminopropyl)carbodiimide hydrochloride; and propylene oxide, diepoxy compounds, and condensing agents capable of forming a chemical bond with a hydroxyl, carboxyl, amino, thiol, or imidazole group, or the like. Moreover, the gelatin can also be cross-linked by heat treatment or UV irradiation. Moreover, these cross-linking methods can also be used in combination. Furthermore, the hydrogel may be prepared by physical cross-linking using salt bridge, electrostatic interaction, hydrogen bond, hydrophobic interaction, or the like.

The degree of gelatin cross-linking in the gelatin hydrogel used in the present invention can be set appropriately according to a bioabsorbable level to be imparted to the gelatin hydrogel. When the cross-linking in the gelatin hydrogel is performed using a cross-linking agent, examples of the concentrations of the gelatin in the gelatin hydrogel and the cross-linking agent include 1 to 20 wt % gelatin and 0.01 to 1 wt % cross-linking agent. The conditions of the cross-linking reaction are not particularly limited, and the reaction can be performed, for example, at 0 to 40° C. for 1 to 48 hours. In general, with increase in the concentrations of the gelatin and the cross-linking agent and in cross-linking time, the degree of cross-linking in the hydrogel is increased and its biodegradable level is decreased.

The form of the gelatin hydrogel used in the present invention is not particularly limited as long as it is applicable to a cell transplantation site. Examples thereof include sheet, cylindrical, prismatic, spherical, and particulate forms. Among these forms of the gelatin hydrogel, a sheet form is preferable. Enhancement in the survival of grafted pluripotent stem cells and further improvement in cardiomyocyte regeneration can be achieved by applying the gelatin hydrogel in a sheet form to a cell transplantation site such that the transplanted pluripotent stem cells are covered with the hydrogel.

For the gelatin hydrogel in a sheet form, it is preferred that the gelatin hydrogel should be sutured in advance to a patch applicable to an epicardium (pericardial patch) and constructed such that it can be fixed to the cell transplantation site via the pericardial patch to prevent the gelatin hydrogel from being displaced from the applied cell transplantation site. Any pericardial patch known in the art can be used, and such a pericardial patch is specifically exemplified by Gore-Tex (registered trademark) PTFE (polytetrafluoroethylene) Patch II (manufactured by WL Gore & Associates, Inc.).

The bFGF contained in the gelatin hydrogel used in the present invention may be prepared by various methods for use as long as the bFGF is purified to such an extent that it can be used as a pharmaceutical agent. Moreover, already commercially available products may be used. The bFGF can be produced, for example, by a method comprising culturing bFGF-producing primarily cultured cells or established cell lines and separating and purifying bFGF from the culture supernatant or the like. Alternatively, genes encoding bFGF are incorporated by a genetic engineering approach into appropriate vectors, which are then inserted into appropriate hosts for transformation, and the recombinant bFGF of interest can be obtained from a culture supernatant of the transformants (see e.g., Nature, 342, 440 (1989), Japanese Patent Laid-Open No. 5-111382, and Biochem. Biophys. Res. Commun. 163, 697-973 (1989)). The host cells are not particularly limited, and various host cells used in conventional genetic engineering approaches can be used, for example, E. coli, yeast, insect, silkworm, and animal cells. The bFGF thus obtained may have the substitution, deletion, and/or addition of one or more amino acids in its amino acid sequence or may also have the substitution, deletion, and/or addition of sugar chain (s) as long as it has substantially the same effect as that of natural bFGF.

The gelatin hydrogel used in the present invention can be obtained by: forming a hydrogel containing temporarily cross-linked gelatin; and then adding thereto dropwise an appropriate amount of a bFGF-containing solution such that the gelatin hydrogel is impregnated with the bFGF-containing solution. Furthermore, the gelatin hydrogel used in the present invention can also be obtained by: appropriately cutting a hydrogel containing temporarily cross-linked gelatin into appropriate size and shape; then lyophilizing and sterilizing the cut hydrogel; and adding dropwise an aqueous bFGF solution to the obtained lyophilized gelatin hydrogel such that the hydrogel is impregnated with bFGF. This impregnation procedure is completed usually in 15 minutes to 1 hour at 4 to 37° C., preferably in 15 to 30 minutes at 4 to 25° C., during which the hydrogel swells due to bFGF, which in turn interacts with the gelatin molecule and is immobilized in the gelatin hydrogel through the physical interaction of complexes formed between the bFGF and the gelatin molecule. Probably, not only electrostatic interaction between the bFGF and the gelatin but also other interactions such as hydrophobic bond and hydrogen bond largely contribute to the complex formation therebetween.

The amount of the bFGF contained in the hydrogel used in the present invention can be set appropriately according to the sex or age of an applicable patient, the form of the hydrogel, etc. and is usually exemplified by an amount corresponding to a bFGF dose of 1 to 100 μg, preferably 5 to 50 μg, more preferably 5 to 10 μg, per kg body weight of a patient. Enhancement in the survival of grafted pluripotent stem cells and further efficient cardiomyocyte regeneration can be achieved by meeting such a bFGF dose.

Moreover, in the hydrogel used in the present invention, the ratio of the bFGF to the hydrogel is also determined according to the bFGF dose and gelatin contents, etc. and is usually preferably approximately 5 times or less by weight. More preferable examples of the ratio of the bFGF to the hydrogel include approximately 5 to approximately $1/10^4$ times by weight.

The water content of the hydrogel used in the present invention influences the slow release of bFGF and can therefore be set appropriately to achieve preferable slow release of bFGF. Examples of the water content of the hydrogel include 80 to 99 wt %, preferably 95 to 98 wt %. The water content serves as an index capable of measuring the degree of cross-linking in this hydrogel. The hydrogel having a larger water content has a lower degree of cross-linking and is thus easily degraded. Specifically, the slow release (gradual release) of bFGF depends on the value of this water content.

Pluripotent Stem Cells Derived from Heart Tissue

Donor cells used in the preparation for treating heart disease of the present invention are pluripotent stem cells derived from heart tissue. Such pluripotent stem cells are not particularly limited as long as they are separated from heart tissue and have the ability to self-replicate together with the ability to differentiate at least into cardiomyocytes. The pluripotent stem cells are preferably exemplified by pluripotent stem cells described in the pamphlet of International Publication No. WO 2006/093276.

Specific examples of the pluripotent stem cells derived from heart tissue preferably used in the present invention include pluripotent stem cells that exhibit CD90, CD29, CD73, stro-1, and CD105 positives as cell surface antigen characteristics. These cell surface antigen characteristics are the typical features of mesenchymal stem cells. Thus, such cell surface characteristics become the evidence that cells having the cell surface antigen characteristics are mesenchymal stem cells. Moreover, one example of the pluripotent stem cells derived from heart tissue includes cells that further exhibit, in addition to the cell surface characteristics, c-kit negative, CD45 negative, CD31 negative, CD34 weakly positive, and HLA-MHC class II negative.

The dose of the pluripotent stem cells derived from heart tissue used in the present invention is set to $10 \times 10^5$ cells or less, preferably $8 \times 10^5$ cells or less, more preferably $7 \times 10^5$ cells or less, per kg body weight of a patient. The lower limit of the dose is not particularly limited, and the pluripotent stem cells are generally administered in the range of $1 \times 10^5$ to $10 \times 10^5$ cells, preferably $3 \times 10^5$ to $8 \times 10^5$ cells, more preferably $5 \times 10^5$ to $7 \times 10^5$ cells. In their combined use with the hydrogel, the survival of grafted pluripotent stem cells is improved by setting the dose (particularly, its upper limit) of the pluripotent stem cells within the range. The resulting pluripotent stem cells can exert their useful functions to a maximum extent. On the other hand, if the dose of the pluripotent stem cells exceeds $1 \times 10^6$ cells per kg body weight of a patient, even their combined use with the hydrogel results in the reduced survival of grafted pluripotent stem cells. As a result, their clinically useful differentiation into cardiomyocytes is not observed.

As can be seen from the dose, the ratio between the bFGF and the pluripotent stem cells is preferably at least 1 to 100 μg of the bFGF with respect to the amount of the pluripotent stem cells of $1 \times 10^6$ cells.

The pluripotent stem cells having the cell surface antigen characteristics can also be obtained through steps (i) to (iii) shown below.

<Step (i) Preparation of Cell Suspension>

First, a heart tissue slice collected from a mammal is enzymatically treated to prepare a cell suspension (step (i)).

In the present invention, the heart tissue serving as a source of collection of the pluripotent stem cells is not particularly limited as long as it is derived from mammals. In the present invention, examples of the mammals include mice, rats, guinea pigs, hamsters, rabbits, cats, dogs, sheep, pigs, cow, goats, monkeys, and humans. When the preparation for treating heart disease of the present invention is applied to humans, it is preferred that the heart tissue serving as a source of collection should be derived from humans. Moreover, the site of the heart tissue used in this step is not particularly limited.

The collection of the heart tissue slice from a mammal is performed by excising the heart tissue slice by usual surgical approaches. Moreover, it is preferred that tissue other than heart tissue (e.g., blood vessels and nerve tissue) should be removed as much as possible from the excised heart tissue slice, prior to the enzymatic treatment. It is also preferred, for enhancing the efficiency of the enzymatic treatment, that the collected heart tissue slice should be chopped into fragments of approximately 1 $mm^3$ or smaller and then enzymatically treated.

Moreover, the enzymatic treatment is performed using an enzyme generally used for preparing a cell suspension from a biological tissue slice. Specific examples of the enzyme used include proteases such as collagenase, trypsin, chymotrypsin, and pepsin. Among them, collagenase is preferable. Such collagenase is specifically exemplified by collagenase type 2 (manufactured by Worthington Biochemical Corp.; 205 U/mg). In the present specification, 1 U collagenase represents an enzyme amount that allows 1 μmol of L-leucine to be released from collagen at 37° C. for 5 hours at pH 7.5.

Moreover, the enzymatic treatment conditions are not particularly limited, and one example thereof includes the following enzymatic treatment conditions:

Enzyme concentration: for example, when collagenase type 2 (manufactured by Worthington Biochemical Corp.; 205 U/mg) is used, examples of its concentration include: usually 0.1 to 0.3 wt %, preferably approximately 0.2 wt %, for treating mouse-derived myocardial tissue; and usually 0.2 to 0.6 wt %, preferably approximately 0.4 wt %, for treating human-derived myocardial tissue. Alternatively, examples of the enzyme concentration include concentrations of usually 4100 to 12300 U, preferably approximately 8200 U, per 100 mg of myocardial tissue.

Treatment temperature: examples thereof usually include a temperature of approximately 37° C.

Treatment time and the number of treatments: examples thereof include enzymatic treatment repeated twice under conditions involving usually a treatment time of 20 to 30 minutes, preferably a treatment time of approximately 20 minutes.

It is preferred that the cell suspension thus obtained by the enzymatic treatment should be centrifuged and after removal of the supernatant, supplemented with a medium suitable for cell growth. Examples of the medium suitable for cell growth include Dulbecco's Modified Eagle Medium (DMEM) containing 10 vol % fetal bovine serum (FBS) and 1 vol % penicillin-streptomycin (mixture of 5000 U/ml penicillin and 5000 μg/ml streptomycin sulfate).

<Step (ii) Separation of Heart Tissue-Derived Cell Group>

Subsequently, from the cell suspension, a heart tissue-derived cell group is separated by a density gradient method (step (ii)).

In this step, the separation of a heart tissue-derived cell group can be performed by density gradient methods usually adopted for cell separation. One example of the separation of a heart tissue-derived cell group according to a preferable embodiment includes a method comprising separating a heart tissue-derived cell group by Percoll density gradient centrifugation. The Percoll density gradient centrifugation is a centrifugation method known in the art using Percoll, one of silica gels, and can separate the cells through centrifugal force without destroying the cells because Percoll is used in layers.

For separating a heart tissue-derived cell group containing the stem cells of interest from the cell suspension by Percoll density gradient centrifugation, for example, the cell suspension can be subjected to differential centrifugation at 1000 G at room temperature for 20 minutes in a discontinuous density gradient comprising 30 vol % and 70 vol % Percoll solutions. As a result, the heart tissue-derived cell group containing the stem cells of interest is obtained at the interface between the 30 vol % and 70 vol % Percoll solutions.

<Step (iii) Separation of Pluripotent Stem Cells>

Subsequently, the heart tissue-derived cell group obtained in the step (ii) is suspension-cultured in a medium containing an epidermal growth factor (EGF) and a basic fibroblast growth factor (bFGF), and cells forming a floating sphere (cell mass) are then selected and separated (step (iii)).

It is preferred that the heart tissue-derived cell group obtained in the step (ii) should further be enzymatically treated, prior to the suspension culture, to eliminate cell-to-cell bonds or adhesion. Specific methods for such enzymatic treatment are not particularly limited, and the enzymatic treatment can be performed by methods known in the art using protease or the like. One example of the enzymatic treatment includes a method comprising treating the heart tissue-derived cell group at 37° C. for approximately 10 minutes with a solution containing 0.05 wt % trypsin and 0.53 mM EDTA. Moreover, after the enzymatic treatment, it is preferred that a protease inhibitor should be added, for inactivation of protease activity, to the heart tissue-derived cell group, which is then used in this step (iii).

The medium used in this step needs only to be a medium used in usual cell culture (suspension culture) supplemented with an epidermal growth factor and bFGF. The medium is preferably exemplified by a human serum- or bovine serum albumin-containing DMEM/F12Ham medium supplemented with the epidermal growth factor and the bFGF. Moreover, the medium used in this step may optionally contain: antibiotics such as streptomycin, kanamycin, and penicillin; B27 Supplement (manufactured by GIBCO); HEPES (5 mM); and the like.

Moreover, the proportions of the epidermal growth factor and the bFGF added to the medium in this step are exemplified by 10 to 20 ng/ml, preferably approximately 20 ng/ml of the epidermal growth factor and 10 to 40 ng/ml, preferably approximately 40 ng/ml of the bFGF.

In this step, the culture is preferably performed by setting the cell concentration at the start of culture to $1\times10^4$ to $2\times10^4$ cells/ml, preferably $2\times10^4$ cells/ml.

The suspension culture in this step is performed usually at 37° C. in a 5% $CO_2$ atmosphere, usually for 14 to 21 days, preferably 14 days.

By such culture, pluripotent stem cells repeat cell division to form a sphere (cell mass), which in turn floats in the culture solution. Thus, the pluripotent stem cells of interest can be obtained by collecting this sphere.

Moreover, the pluripotent stem cells having the cell surface antigen characteristics can be obtained not only by the method comprising the steps (i) to (iii) but also by a method comprising performing the steps (i) and (ii) and then separating, by fractionation approaches known in the art, cells having the cell surface antigen characteristics from the heart tissue-derived cell group obtained in the step (ii). One example of such cell fractionation approaches includes a method using a flow cytometer provided with sorting functions.

The pluripotent stem cells can be proliferated by culture in a medium containing an epidermal growth factor and bFGF. It is preferred that the sphere obtained in the step (iii) should be treated, prior to the culture, with protease for sphere degradation to obtain floating pluripotent stem cells. Methods for obtaining such floating pluripotent stem cells are exemplified by methods comprising treating the sphere with trypsin at a concentration of 0.05 wt % at 37° C. for approximately 20 minutes. After the protease treatment, it is preferred that a protease inhibitor should be added to the cells to inhibit protease activity. The medium used in this culture is the same as that used in the step (iii). Specifically, the pluripotent stem cells can be proliferated into the desired amount by culture at a cell concentration of 20 cells/μl (at the start of culture) at 37° C. in a 5% $CO_2$ atmosphere, usually for 14 to 21 days.

Furthermore, it is preferred that the pluripotent stem cells of the present invention should be cells prepared from the myocardial tissue of a patient in need of administration of the preparation for treating heart disease of the present invention. However, the pluripotent stem cells may be prepared from myocardial tissue other than that of the patient as long as they can be transplanted. For example, isolated pluripotent stem cells can be subcultured to prepare an established line. Using such an established line, cell therapy can be performed even on the aged or the like from which autologous cells are hardly obtained.

Specific Embodiment of Preparation for Treating Heart Disease

The preparation for treating heart disease of the present invention may be a pharmaceutical composition in a mixed form obtained by mixing the hydrogel and the pluripotent stem cells in advance as long as it comprises both these components in combination. However, the preparation for treating heart disease of the present invention is preferably a kit comprising these components that are not mixed. In the former case (i.e., the pharmaceutical composition in a mixed form), the hydrogel in a particulate form is preferably used from the viewpoint of uniformly mixing the hydrogel and the pluripotent stem cells. Alternatively, in the latter case (i.e., the kit), the form of the hydrogel is not particularly limited.

When the preparation for treating heart disease of the present invention is the pharmaceutical composition in a mixed form, this preparation is injected for administration to the heart disease site of a patient by means of a catheter or incision.

Alternatively, when the preparation for treating heart disease of the present invention is the kit, this preparation may be administered by any approach such as coadministration of the hydrogel and the pluripotent stem cells, administration of the pluripotent stem cells, followed by the hydrogel, or administration of the hydrogel, followed by the pluripotent stem cells. Examples of such an approach according to a preferable aspect include a method comprising administering the pluripotent stem cells and then applying the hydrogel in a sheet form such that the pluripotent stem cell-administered site (cell transplantation site) is covered with the hydrogel. Moreover, when this hydrogel in a sheet form is immobilized in advance on a non-biodegradable polymer support for use, the hydrogel can be fixed to the administration site via the polymer support. As a result, the hydrogel can be prevented from being displaced after operation, while the cells can be prevented from being diffused. The survival of the resulting grafted pluripotent stem cells can be improved further markedly. Examples of the non-biodegradable polymer support currently available clinically include, but not limited to, Gore-Tex (registered trademark) polytetrafluoroethylene pericardial patches (manufactured by Gore & Associates, Inc.).

In the preparation for treating heart disease of the present invention, the hydrogel, the pluripotent stem cells, or a mixture thereof may be diluted appropriately with a pharmaceutically acceptable carrier, if necessary, from the viewpoint of simple administration, the safety of the pluripotent cells, etc. For example, saline or a buffer is used as the pharmaceutically acceptable carrier.

Moreover, the preparation for treating heart disease of the present invention can be administered to a heart disease site by a method appropriately selected according to the form of the hydrogel, etc., from among a method using a catheter, a method using thoracic incision, and the like.

Examples of the heart disease targeted by the preparation for treating heart disease of the present invention include heart diseases that cause myocardial or coronary disorder and reduce the force of heart contraction, and specifically include myocardial infarction, dilated cardiomyopathy, ischemic heart disease, and congestive heart failure.

Synergistic Myocardial Regeneration Effect and Safety

The bFGF-induced effect of proliferating the pluripotent stem cells derived from heart tissue is much higher than that induced by other growth factors, as shown in Examples described later. Thus, the combined use of the pluripotent stem cells derived from heart tissue with bFGF is much more highly effective than that of bone marrow stem cells with bFGF. In actuality, even cells having pluripotency do not always have the high degree of differentiation into cardiomyocytes. Moreover, cell therapy in the heart cannot exert expected effect unless vascular cells are regenerated by the differentiated cells. In fact, the clinical trials of cell therapy in the heart have failed using bone marrow stem cells or skeletal myoblasts.

The present inventors have identified pluripotent stem cells derived from heart tissue and bFGF as the best combination from among various options. This combination is not a simple combination of matters known in the art. The excellent effect of the preparation for treating heart disease of the present invention is synergistic effect brought about by the interaction between the high degree of differentiation of the heart tissue-derived pluripotent stem cells into cardiomyocytes and the bFGF (slowly released from the hydrogel)-induced sustained effect of improving cardiovascular cell regeneration.

Although embryonic stem cells or iPS cells usually have teratoma problems, the combined use of pluripotent stem cells derived from heart tissue (i.e., tissue stem cells) and bFGF does not cause the complication of teratoma. Moreover, the pluripotent stem cells of the present invention exhibit the features of mesenchymal stem cells and therefore, can hardly cause immune rejection. Specifically, the preparation for treating heart disease of the present invention is also excellent in safety.

EXAMPLES

Hereinafter, the present invention will be described in detail with reference to Examples. However, the present invention is not intended to be limited to them.

Example 1

Preparation of bFGF-Containing Gelatin Hydrogel

Acidic gelatin with a concentration of 10 wt % was chemically cross-linked with glutaraldehyde, and the cross-linking agent was then inactivated. Next, the gelatin was washed with distilled water several times to obtain a cross-linked gelatin hydrogel in a sheet form of approximately 0.3 to 0.4 mm in thickness having a water content of 75%. Subsequently, sterilized distilled water containing 200 µg of bFGF was added dropwise thereto such that the gelatin hydrogel was impregnated with an appropriate amount of the aqueous bFGF solution to obtain a bFGF-containing gelatin hydrogel in a sheet form.

The obtained bFGF-containing gelatin hydrogel in a sheet form was cut into pieces of 5×5 cm square. The bFGF content of the obtained bFGF-containing gelatin hydrogel is adjusted such that the dose of the bFGF is 5 to 6 µg/kg per sheet. This bFGF-containing gelatin hydrogel in a sheet form was preliminarily sutured to the central part of a Gore-Tex (registered trademark) PTFE (polytetrafluoroethylene) pericardial patch (6×6 cm; manufactured by Gore & Associates, Inc.).

Example 2

Obtainment of Human Heart Tissue-Derived Pluripotent Stem Cells and Confirmation of Ability of the Pluripotent Stem Cells to Differentiate into Each Cardiomyocyte (1) Preparation of Cell Suspension Heart tissue slices collected from humans were placed in a cold PBS (phosphate-buffered saline)-containing petri dish on ice and stirred to remove blood from the heart tissue slices. Subsequently, the heart tissue slices were washed in a petri dish containing fresh cold PBS. Furthermore, this washing of the heart tissue slices was repeated twice, and the PBS was finally removed. Then, the homogenized heart tissue fragments were chopped into approximately 1 $mm^3$ or smaller using sterilized scissors. The chopped heart tissue slices (approximately 10 mg) were transferred to a 100-ml Erlenmeyer flask, to which 20 ml of a solution containing 0.2 wt % collagenase type 2 (manufactured by Worthington Biochemical Corp.) was further added, and the heart tissue slices were enzymatically treated by shaking for 20 minutes in a thermostat bath set to 37° C. Subsequently, the heart tissue slices were well stirred by further pipetting at a speed of 3 ml/sec using a 10-ml electric pipetter. Then, 2.2 ml of a solution containing 0.1 wt % DNase I (manufactured by Worthington Biochemical Corp.) was further added thereto, and the solution was shaken for 3 minutes in a thermostat bath set to 37° C. After such enzymatic treatment, the enzyme was neutralized by the addition of 20 ml of a DMEM (manufactured by GIBCO) medium containing 10 vol % FBS (fetal bovine serum) (manufactured by Thermo Scientific Hyclone) and 1 vol % penicillin-streptomycin (hereinafter, this medium is referred to as a "medium 1") to prepare a cell-containing solution. Then, the cell-containing solution was filtered using a 70-µm cell strainer (manufactured by BD FALCON) and a 40-µm cell strainer (manufactured by BD FALCON). The cell-containing solution thus filtered was centrifuged at 1500 rpm for 5 minutes and after removal of the supernatant thereof, supplemented with 10 ml of the medium 1 to prepare a cell suspension (hereinafter, referred to as a cell suspension 1), which was then stored in ice. Moreover, the same treatment was performed again on the heart tissue slices remaining in the 100-ml Erlenmeyer flask to prepare a cell suspension (hereinafter, referred to as a cell suspension 2) in the same way as above. The cell suspensions 1 and 2 thus obtained were mixed and subjected to steps described below.

(2) Separation of Heart Tissue-Derived Cell Group by Percoll Density Gradient Centrifugation A solution with an undiluted Percoll solution (manufactured by Amersham Biosciences Corp.): 10×PBS (−) (manufactured by GIBCO) ratio of 9:1 by volume was used as a Percoll stock. The Percoll stock was diluted with 1×PBS (−) (manufactured by GIBCO) to prepare solutions with a Percoll stock concentration of 30 vol % or 70 vol %. The 30 vol % Percoll solution was stained by the addition of 0.1 vol % phenol red (manufactured by SIGMA-ALDRICH CORP.). First, 3 ml of the 30 vol % Percoll solution was poured to a 15-ml conical tube, to which the 70 vol % Percoll solution was then carefully added using an electric pipetter such that the 70 vol % Percoll solution was layered below the 30 vol % Percoll solution. Subsequently, 3 ml of the human heart tissue-derived cell suspension was carefully layered above the 30 vol % Percoll solution. The conical tube was centrifuged at 1000 G at room temperature for 20 minutes, with as slow acceleration and deceleration as possible. After the centrifugation, the cell population of interest was confirmed to be distributed at the interface between the 30 vol % and 70 vol % Percoll solutions. It was also confirmed that blood cell components were distributed at the bottom, and mainly cell debris was distributed above the 30 vol % Percoll layer. The cell debris was first removed using a Pasteur pipette, and the cell population of interest present at the interface was then collected into a 50-ml conical tube using another pipette. To the conical tube, 30 ml of a DMEM/F12Ham (manufactured by GIBCO) medium was added. The mixture was sufficiently stirred and then centrifuged, and the supernatant was removed. Subsequently, 1 ml of a trypsin-EDTA solution (containing 0.05 wt % trypsin and 0.53 mM EDTA-4Na) (manufactured by GIBCO) was added thereto, and the tube was shaken for 10 minutes in a thermostat bath set to 37° C. to eliminate cell-to-cell agglutination or bonds. Subsequently, 500 µl of a trypsin inhibitor (manufactured by Roche Diagnostics Corp.) was added thereto, and the cells were sufficiently suspended by the further addition of 8.5 ml of a DMEM/F12Ham medium (manufactured by GIBCO). Then, the number of cells was counted using a hemacytometer.

(3) Sphere Formation

The human heart tissue-derived cell group obtained in the paragraph (2) was suspension-cultured at 37° C. for 14 days in a 5% $CO_2$ atmosphere on a noncoated cell culture dish (manufactured by Becton, Dickinson and Company) using a mouse expansion medium [containing DMEM/F12Ham (manufactured by GIBCO), 2 wt % B27 Supplement (manufactured by GIBCO), 1 vol % penicillin-streptomycin, 40 ng/ml recombinant human basic FGF (manufactured by Promega Corp.), and 20 ng/ml mouse EGF (manufactured by SIGMA-ALDRICH CORP.)]. In this context, the cell concentration at the start of culture was set to $2.0 \times 10^4$ cells/ml.

FIG. 1 shows a microscope photograph taken of spheres floating in the culture solution after 1 day and 7 days of culture. After the culture, the spheres were collected to obtain human heart tissue-derived sphere-forming cells (pluripotent stem cells).

(4) Proliferation of Sphere-Forming Cells

The collected spheres were placed in 2 ml of a DMEM/F12Ham (manufactured by GIBCO) medium. The mixture was well mixed and then centrifuged (4° C., 1500 rpm, 5 minutes), and the supernatant was sufficiently removed. Subsequently, 1 ml of a trypsin-EDTA solution (containing 0.05 wt % trypsin and 0.53 mM EDTA-4Na) (manufactured by GIBCO) was added thereto, and the spheres were degraded by shaking for 20 minutes in a thermostat bath set to 37° C. such that cells forming the spheres (hereinafter, referred to as sphere-forming cells) floated. Subsequently, the cells were sufficiently suspended by the addition of 500 µl of a trypsin inhibitor (manufactured by Roche Diagnostics Corp.). Then, the number of cells was counted using a hemacytometer.

The sphere-forming cells thus suspended were cultured at a cell concentration of 20 cells/µl (at the start of culture) at 37° C. for 3 days in a 5% $CO_2$ atmosphere on a fibronectin-coated cell culture dish using a mouse expansion medium [containing DMEM/F12Ham (manufactured by GIBCO), 2 wt % B27 Supplement (manufactured by GIBCO), 1 vol % penicillin-streptomycin, 40 ng/ml recombinant human basic FGF (manufactured by Promega Corp.), and 20 ng/ml mouse EGF (manufactured by SIGMA-ALDRICH CORP.)].

Figure 2:
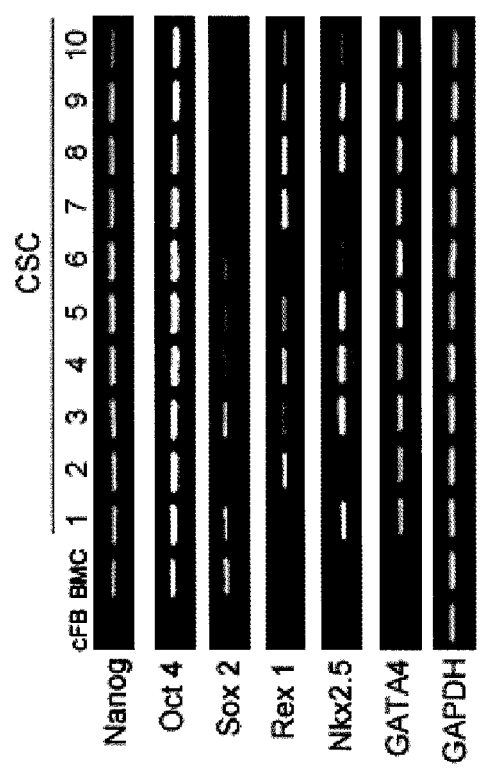
FIG. 2 is a diagram showing the results of PCR-analyzing the expression of various markers (Rex 1, Oct 4, Nanog, Nkx-2.5, Sox 2, and GATA-4) in 10 different lines of human-derived sphere-forming cells (CSC: cardiac stem cell). cFB represents a cardiac fibroblast, and BMC represents a bone marrow-derived mesenchymal stem cell.

The sphere-forming cells thus cultured were analyzed by PCR for their expression of various markers (Rex 1, Nkx-2.5, Oct 4, Nanog, GATA-4, and Sox 2). The obtained results are shown in FIG. 2. The results demonstrated that the human heart tissue-derived sphere-forming cells have the same differentiation property as that of ectodermal or embryonic stem cells.

Figure 3:
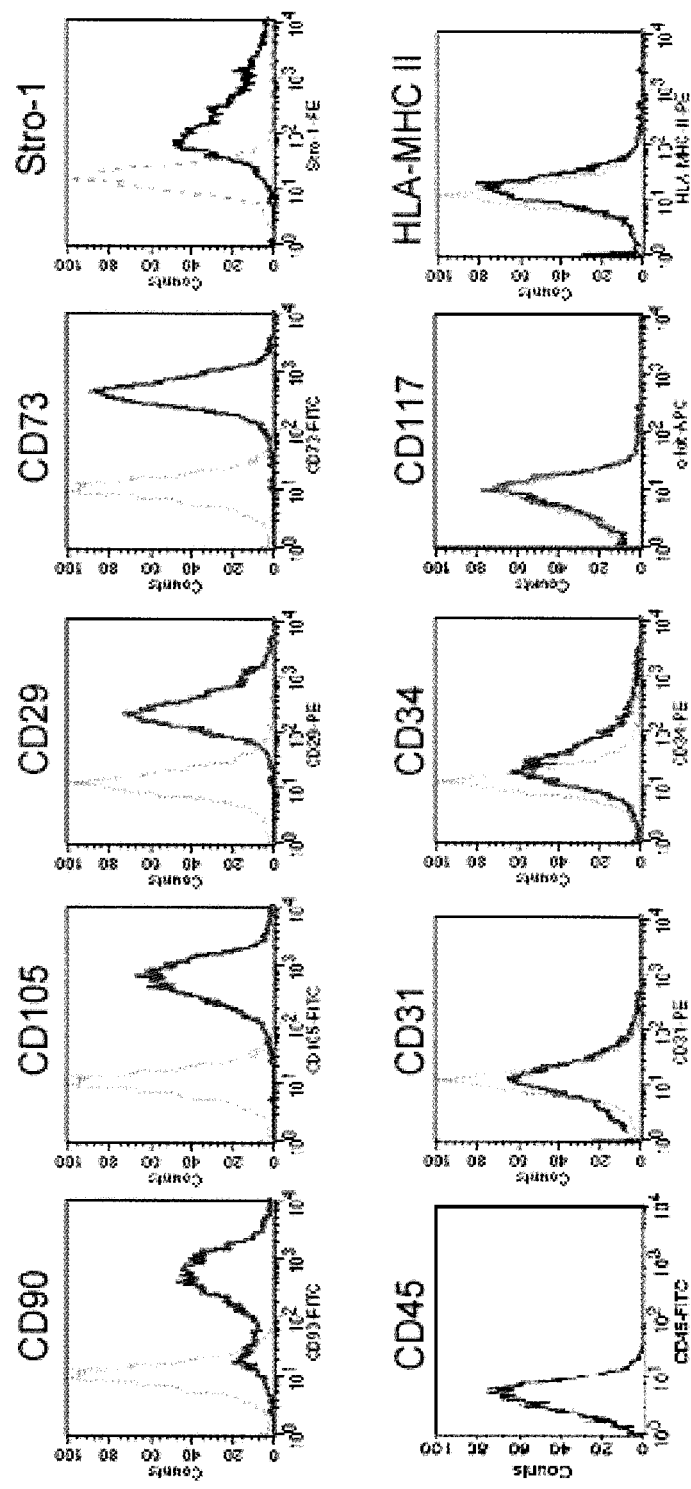
FIG. 3 shows the results of FACS-analyzing various cell surface antigens (c-kit (CD117), CD34, CD90, CD105, CD29, CD73, Stro-1, CD45, CD31, and HLA-MHC class II) in human-derived sphere-forming cells. In the diagram, the thick (heavy) lines represent the analysis results of the sphere-forming cells, and the thin (light) lines represent the analysis results of a control (unlabeled cells)

Moreover, the proliferated sphere-forming cells were analyzed for various cell surface antigens c-kit, CD45, CD31, CD34, HLA-MHC class II, CD90, CD29, CD73, stro-1, and CD105. The analysis results are shown in FIG. 3. The results demonstrated that the human-derived sphere-forming cells are c-kit-negative, CD45-negative, CD31-negative, CD34-weakly positive, HLA-MHC class II-negative, CD90-positive, CD29-positive, CD73-positive, stro-1-positive, and CD105-positive.

(5) Confirmation of Differentiation of Sphere-Forming Cells into Cardiomyocytes

The sphere-forming cells proliferated in the paragraph (4) were collected by centrifugation and induced to differentiate into cardiomyocytes by culture at 37° C. for 21 days in a 5% $CO_2$ atmosphere in an MEM medium (manufactured by GIBCO) containing $1 \times 10^{-8}$ mol/l dexamethasone and 1 vol % penicillin-streptomycin. As a result, it was confirmed that the human heart tissue-derived sphere-forming cells differentiate into beating cardiomyocytes. This differentiation into cardiomyocytes was also confirmed from analysis results shown below.

<Analysis by Human Cardiac Muscle-Specific Troponin-T Staining>

Figure 4:
FIG. 4 is a photograph of cardiomyocytes differentiated from human-derived sphere-forming cells.

The cells thus induced to differentiate were stained with human cardiac muscle-specific troponin-T and observed. As a result, the presence of cardiomyocytes was confirmed (see FIG. 4).

<Analysis by PCR>

Figure 5:
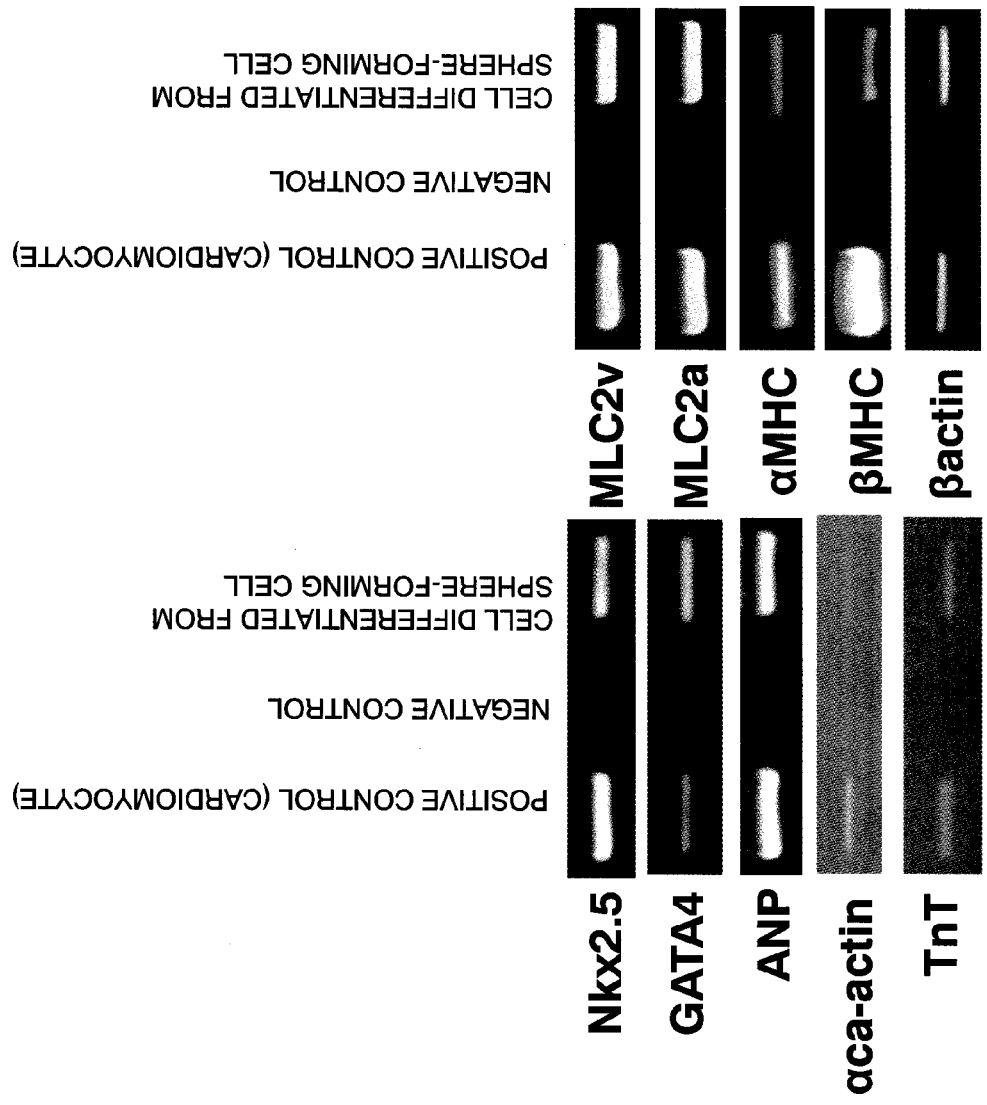
FIG. 5 is a diagram showing the results of PCR-analyzing the expression of various markers (Nkx-2.5, GATA4, ANP, $\alpha$-ca-actin, TnT, MLC2v, MLC2a, $\alpha$-MHC ($\alpha$-myosin heavy chain), and $\beta$-MHC ($\beta$-myosin heavy chain)) in cardiomyocytes differentiated from human-derived sphere-forming cells. In this analysis, $\beta$-actin was used as a control.

The cells after 21 days into differentiation induction were analyzed by PCR for their expression of various markers (Nkx-2.5, GATA4, ANP, α-ca-actin, TnT, MLC2v, MLC2a, α-MHC (α-myosin heavy chain), β-MHC (β-myosin heavy chain), and β-actin). The obtained results are shown in FIG. 5. As can be seen from FIG. 5, these various markers were expressed in the cells thus cultured in the presence of dexamethasone, demonstrating successful differentiation of the human heart tissue-derived sphere-forming cells into cardiomyocytes.

(6) Results

The results shown above revealed that the obtained sphere-forming cells have the ability to self-replicate together with the property of differentiating at least into cardiomyocytes and are pluripotent stem cells useful as myocardial stem cells.

Example 3

Preparation of Miniature Pigs with Myocardial Infarction and Treatment (1) Preparation of Miniature Pigs with Myocardial Infarction The left coronary arteries of miniature pigs (approximately 30 kg, 8-week-old female) were blocked for 90 minutes using a subcutaneous balloon catheter and then reopened. Subsequently, the resulting pigs were raised for 28 days to prepare miniature pigs with myocardial infarction whose left ventricular ejection fraction (LVEF) was decreased from approximately 60% to 35 to 45%. Using the miniature pigs with myocardial infarction thus raised for 28 days, treatment shown below was conducted.

Figure 6:
FIG. 6 is a photograph of a bFGF-containing gelatin hydrogel that was preliminarily sutured to the central part of a Gore-Tex (registered trademark) PTFE (polytetrafluoroethylene) pericardial patch (6×6 cm; manufactured by WL Gore & Associates, Inc.) and then sutured to a myocardial ischemia site.

(2) Administration of bFGF-Containing Gelatin Hydrogel and Pluripotent Stem Cells to Miniature Pigs with Myocardial Infarction The miniature pigs with myocardial infarction thus prepared were divided into the following 5 groups, and their myocardial infarction was treated:

Group A (n=10): thoracic incision was made in the miniature pigs, and their cardiac muscles with infarction were administered with 3 ml of a DMEM medium per kg body weight of the miniature pigs and then covered with the bFGF-containing gelatin hydrogel (dose: 5 to 6 μg/kg) in a sheet form sutured to the pericardial patch, which was then sutured in place, as shown in FIG. 6.

Group B (n=10): thoracic incision was made in the miniature pigs, and their cardiac muscles with infarction were administered with a DMEM medium suspension of the heart tissue-derived pluripotent stem cells at a dose of $5 \times 10^5$ to $6 \times 10^5$ cells per kg body weight of the miniature pigs, whereas the bFGF-containing gelatin hydrogel in a sheet form was not administered thereto.

Group C (n=10): thoracic incision was made in the miniature pigs, and their cardiac muscles with infarction were administered with a DMEM medium suspension of bone marrow-derived mesenchymal stem cells (RIKEN CELL BANK, RCB HMS0008, HMS0043, HMS0019, HMS0021, HMS0024, HMS0048, HMS0049) at a dose of $5 \times 10^5$ to $6 \times 10^5$ cells per kg body weight of the miniature pigs and then covered with the bFGF-containing gelatin hydrogel (dose: 5 to 6 μg/kg) in a sheet form sutured to the pericardial patch, which was then sutured in place.

Group D (n=10): thoracic incision was made in the miniature pigs, and their cardiac muscles with infarction were administered with a DMEM medium suspension of the heart tissue-derived pluripotent stem cells at a dose of $5 \times 10^5$ to $6 \times 10^5$ cells per kg body weight of the miniature pigs and then covered with the bFGF-containing gelatin hydrogel (dose: 5 to 6 μg/kg) in a sheet form sutured to the pericardial patch, which was then sutured in place.

Group E (n=10): thoracic incision was made in the miniature pigs, and their cardiac muscles with infarction were administered with a DMEM medium suspension of the heart tissue-derived pluripotent stem cells at a dose of $5 \times 10^6$ to $6 \times 10^6$ cells per kg body weight of the miniature pigs and then covered with the bFGF-containing gelatin hydrogel (dose: 5 to 6 μg/kg) in a sheet form sutured to the pericardial patch, which was then sutured in place.

(3) Evaluation of Therapeutic Effect on Miniature Pigs with Myocardial Infarction The miniature pigs with myocardial infarction were raised for 28 days after the transplantation therapy of the paragraph (2) and evaluated for items shown below to determine the therapeutic effect on the myocardial infarction in the miniature pigs.

<Evaluation of Survival of Grafted Pluripotent Stem Cells in Host Cardiac Muscles>

4 and 28 days after transplantation therapy, the donor cells (heart tissue-derived pluripotent stem cells described above) grafted in the host cardiac muscles were labeled with SPIO (superparamagnetic iron oxide), followed by iron staining. By this staining, the pluripotent stem cells are stained brown, and their shadows are visualized as block colors in MRI. Based on these staining results, the survival of grafted pluripotent stem cells in the host cardiac muscles was determined.

Figure 7:
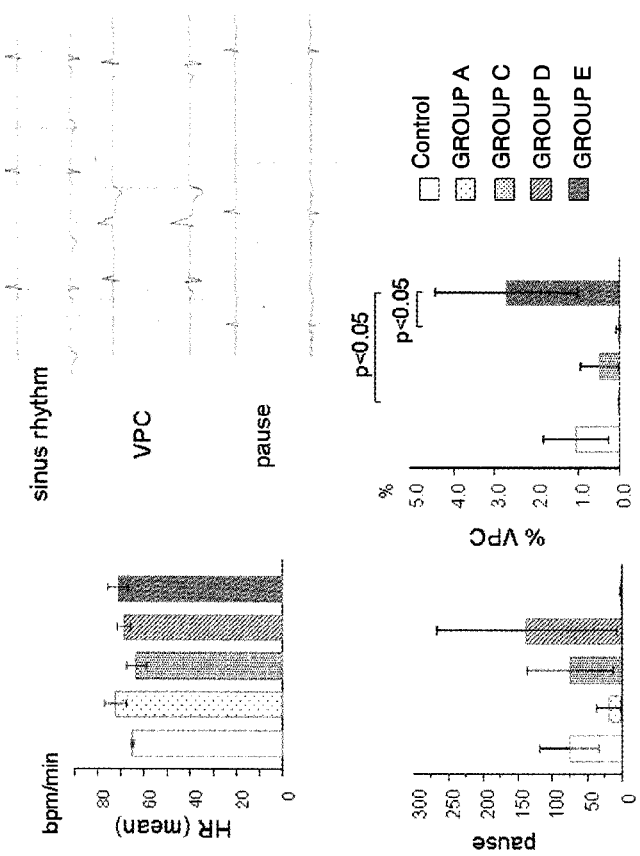
FIG. 7 is a diagram showing the results of evaluating the survival of grafted pluripotent stem cells in host cardiac muscles. The upper box shows the results of labeling pluripotent stem cells derived from heart tissue with SPIO, followed by iron staining. The lower left boxes respectively show an MRI image to visualize pluripotent stem cells successfully grafted in a myocardial infarction site 4 and 28 days after transplantation therapy in groups B and D. The lower right graph shows the proportion of pluripotent stem cells successfully grafted (SPIO survival ratio) in a myocardial infarction site 28 days after transplantation therapy in groups B and D.

The results are shown in FIG. 7. The upper box of FIG. 7 shows the results of labeling the pluripotent stem cells derived from heart tissue with SPIO, followed by iron staining. The lower left boxes of FIG. 7 respectively show an MRI image to visualize pluripotent stem cells successfully grafted in a myocardial infarction site 4 and 28 days after transplantation therapy in the groups B and D. Moreover, the lower right graph of FIG. 7 shows the proportion of pluripotent stem cells successfully grafted (SPIO survival ratio) in a myocardial infarction site 28 days after transplantation therapy in the groups B and D. These results demonstrated that the combined administration of the bFGF-containing gelatin hydrogel and the pluripotent stem cells (dose: $5 \times 10^5$ to $6 \times 10^5$ cells/kg) significantly improves the survival of the graft in the host cardiac muscles, compared with the single administration of the pluripotent stem cells (dose: $5 \times 10^5$ to $6 \times 10^5$ cells/kg).

<Examination of Arrhythmogenic Effect>

Figure 8:
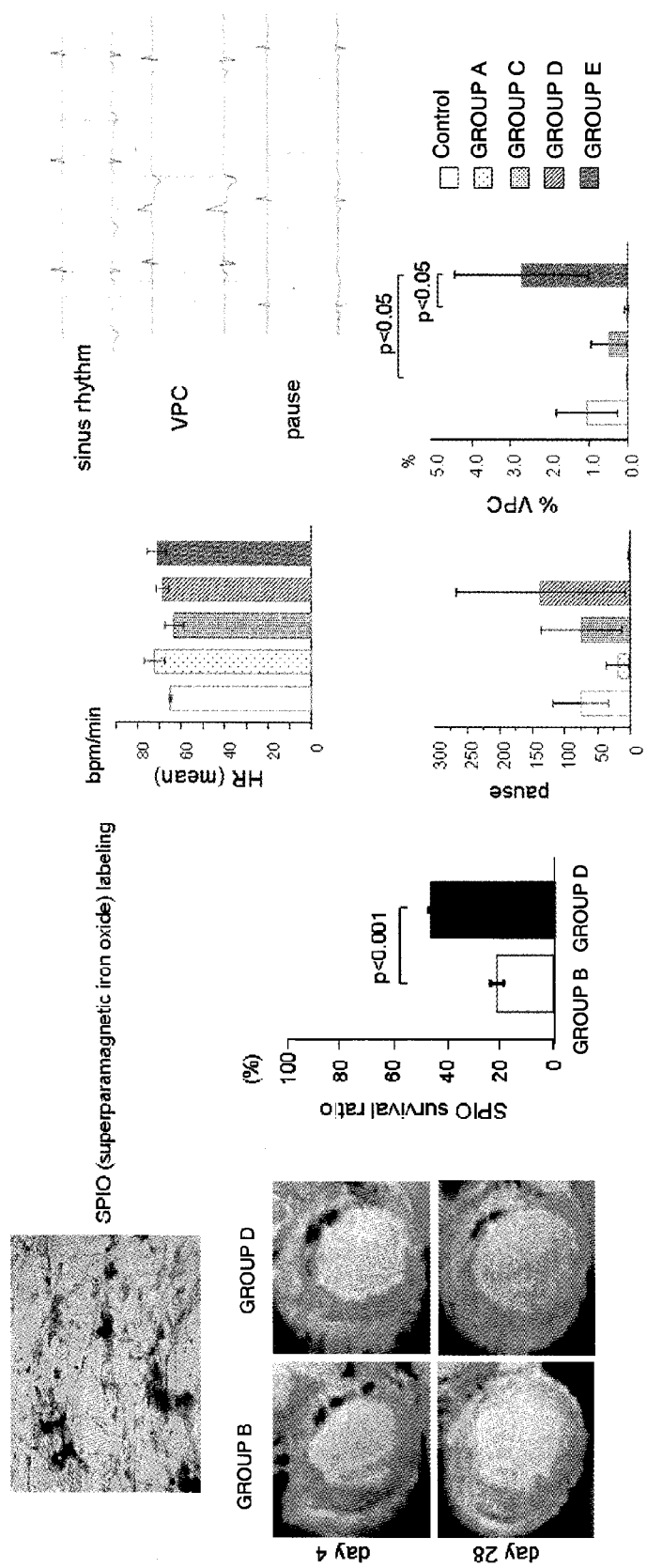
FIG. 8 is a diagram showing the results of examining arrhythmogenic effect. The diagram shows the results of measuring heart rate (HR), pause, and ventricular premature contraction (VPC) in groups A to E. In the diagram, the electrocardiogram represents an electrocardiogram of diagnosed individuals in the group E.

28 days after transplantation therapy, the miniature pigs in each group were electrocardiogram-analyzed to examine arrhythmogenic effect. FIG. 8 shows the results of measuring the heart rate (HR), pause, and ventricular premature contraction (VPC) of the miniature pigs in the groups A to E 28 days after transplantation therapy. As can be seen from FIG. 8, high ventricular premature contraction was observed in the group E administered with the combination of the bFGF-containing gelatin hydrogel and the pluripotent stem cells (dose: $5 \times 10^6$ to $6 \times 10^6$ cells/kg). By contrast, ventricular premature contraction was markedly suppressed in the group D administered with the combination of the bFGF-containing gelatin hydrogel and the pluripotent stem cells (dose: $5\times10^5$ to $6\times10^5$ cells/kg).

<Analysis of Cardiac Functions>

Figures 9, 10:
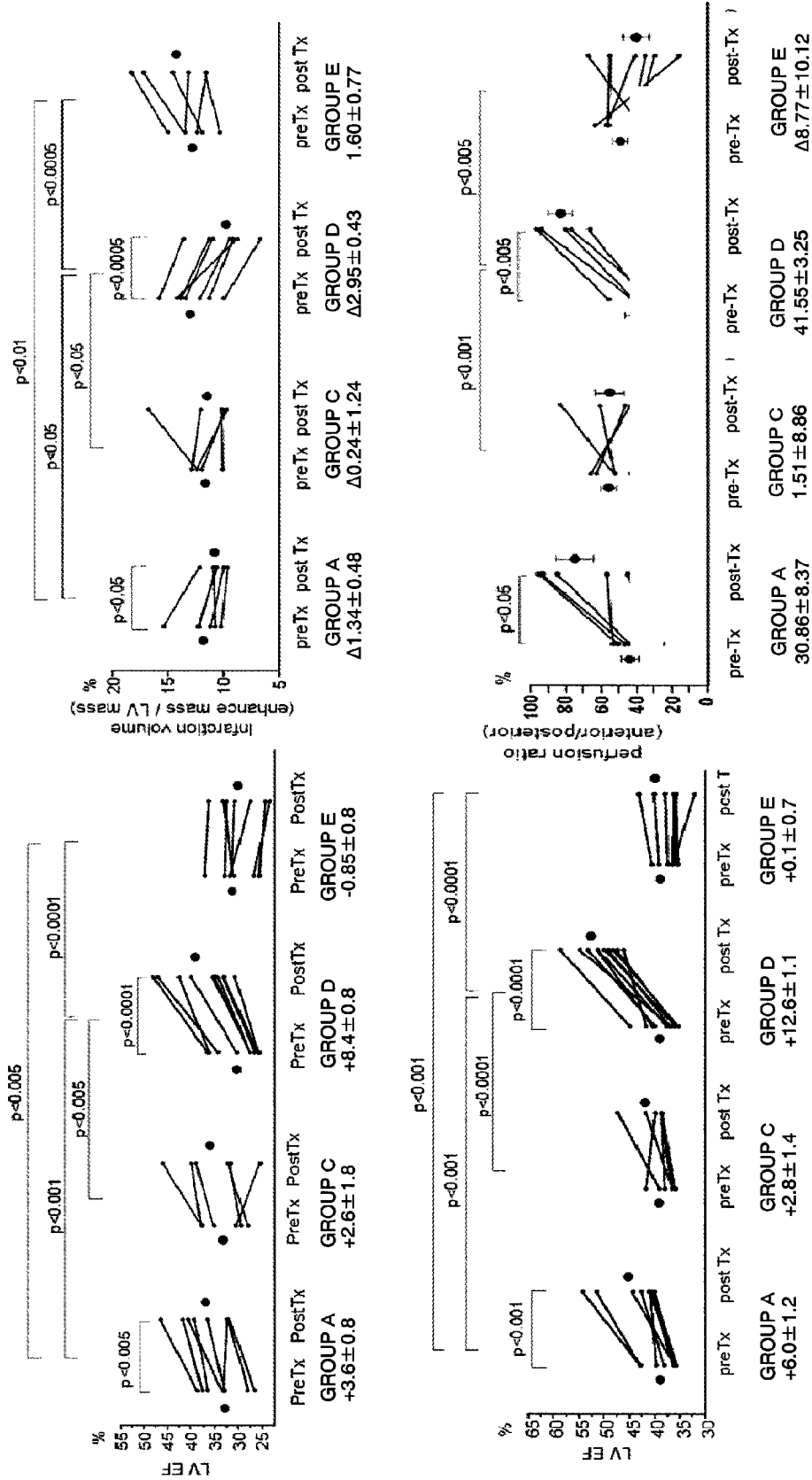
FIG. 9 is a diagram showing the results of analyzing cardiac functions. The upper graph shows the results of measuring a left ventricular ejection fraction (LVEF) by MRI, and the lower graph shows the results of measuring a left ventricular ejection fraction calculated by echocardiography. In the diagram, "Pre Tx" means pretreatment, and "Post Tx" means post-treatment.
FIG. 10 is a diagram showing the results of analyzing the degree of amelioration of infarction size and intramyocardial perfusion at a microvascular level. The upper graph shows the results of measuring infarction size (Infarction volume), and the lower graph shows the results of measuring intramyocardial perfusion at a microvascular level (perfusion ratio). In the diagram, "Pre Tx" means pretreatment, and "Post Tx" means post-treatment.

28 days after transplantation therapy, the miniature pigs in each group were analyzed for their cardiac functions by MRI and echocardiography. The results are shown in FIG. 9. The upper graph of FIG. 9 shows the results of measuring a left ventricular ejection fraction (LVEF) by MRI, and the lower graph of FIG. 9 shows the results of measuring a left ventricular ejection fraction by echocardiography. From these results, marked improvement in cardiac functions was observed only in the group D administered with the combination of the bFGF-containing gelatin hydrogel and the pluripotent stem cells (dose: $5\times10^5$ to $6\times10^5$ cells/kg). By contrast, the significant effect of improving cardiac functions was not observed in the group E administered with the combination of the bFGF-containing gelatin hydrogel and the pluripotent stem cells (dose: $5\times10^6$ to $6\times10^6$ cells/kg).

<Analysis of Degree of Amelioration of Infarction Size and Intramyocardial Perfusion at a Microvascular Level>

28 days after transplantation therapy, the miniature pigs in each group were analyzed for their degree of amelioration of infarction size and intramyocardial perfusion at a microvascular level by contrast MRI and contrast echocardiography. The results are shown in FIG. 10. The upper graph of FIG. 10 shows the results of measuring infarction size (Infarction volume), and the lower graph shows the results of measuring intramyocardial perfusion at a microvascular level (perfusion ratio). As can be seen from FIG. 9, the significant degree of amelioration of infarction size and intramyocardial perfusion at a microvascular level was observed only in the group D administered with the combination of the bFGF-containing gelatin hydrogel and the pluripotent stem cells (dose: $5\times10^5$ to $6\times10^5$ cells/kg). By contrast, merely the degree of amelioration equivalent to that of the group A or B was observed in the group E administered with the combination of the bFGF-containing gelatin hydrogel and the pluripotent stem cells (dose: $5\times10^6$ to $6\times10^6$ cells/kg).

<Analysis of Vascularization>

Figure 11:
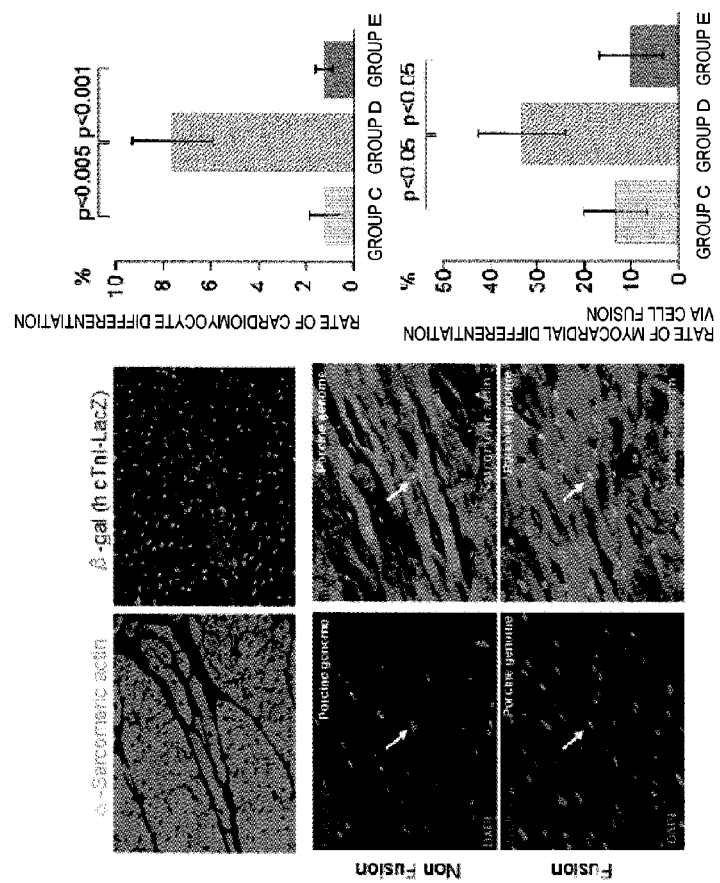
FIG. 11 is a diagram showing the results of analyzing vascularization. The diagram shows the results of measuring each of vascular density of the total infarction site (total), vascular density of the border area of infarction (Border area), vascular density of the central part of infarction (Scar area), vascular density of blood vessels<50 μm in diameter, and vascular density of blood vessels>50 μm in diameter in each group.

28 days after transplantation therapy, the miniature pigs in each group were analyzed for vascularization by vascular density measurement. FIG. 11 shows each of vascular density of the total infarction site (total), vascular density of the border area of infarction (Border area), vascular density of the central part of infarction (Scar area), vascular density of blood vessels<50 μm in diameter, and vascular density of blood vessels>50 μm in diameter in each group.

From these results, the most effective effect of improving blood flow was also observed in the group D administered with the combination of the bFGF-containing gelatin hydrogel and the pluripotent stem cells (dose: $5\times10^5$ to $6\times10^5$ cells/kg).

<Evaluation of Cardiomyocyte Regeneration>

Figure 12:
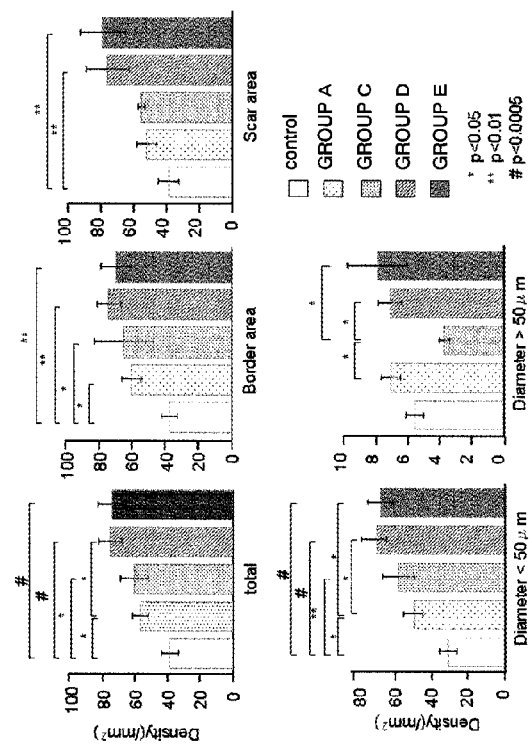
FIG. 12 is a diagram showing the results of evaluating the degree of cardiomyocyte regeneration. In the diagram, the left photographs respectively show the results of staining the cardiac muscles of miniature pig hearts in group D, wherein the cardiac muscles were stained with beta-gal (red; upper box), human Y chromosome (red; middle box), and pig-specific gene probes (yellow; lower box). Moreover, the upper right graph shows the rate of cardiomyocyte differentiation in each group, and the lower right graph shows the rate of myocardial differentiation via cell fusion in each group.

28 days after transplantation therapy, the miniature pigs in each group were evaluated for cardiomyocyte regeneration in the cardiac muscles of their hearts. In the cardiac muscles of the hearts of the miniature pigs in each group, newly regenerated human cardiomyocytes were detected using beta-gal (red) and human Y chromosome (red) under the control of human troponin-I promoters. Moreover, the host pig cardiomyocytes were differentiated therefrom using pig-specific gene probes (yellow). The entire cardiomyocytes and the nuclei were detected based on actin (green) and DAPI (blue), respectively. The results are shown in FIG. 12. The photographs shown in FIG. 12 respectively show the results of staining the cardiac muscles of the miniature pig hearts in the group D, wherein the cardiac muscles were stained with beta-gal (red; upper box), human Y chromosome (red; middle box), and pig-specific gene probes (yellow; lower box). Moreover, in FIG. 12, the upper right graph shows the ratio of pluripotent stem cells differentiated into cardiomyocytes to successfully grafted pluripotent stem cells (rate of cardiomyocyte differentiation), and the lower right graph shows the ratio of pluripotent stem cells differentiated into cardiomyocytes via cell fusion to the pluripotent stem cells differentiated into cardiomyocytes (rate of myocardial differentiation via cell fusion).

These results also demonstrated that the group D administered with the combination of the bFGF-containing gelatin hydrogel and the pluripotent stem cells (dose: $5\times10^5$ to $6\times10^5$ cells/kg) has much more excellent cardiomyocyte regeneration than that of the group C or E.

<Analysis of Morphology of Myocardial Fibrosis and Degree of Macrophage Invasion in Ischemic Heart>

Figures 13, 14:
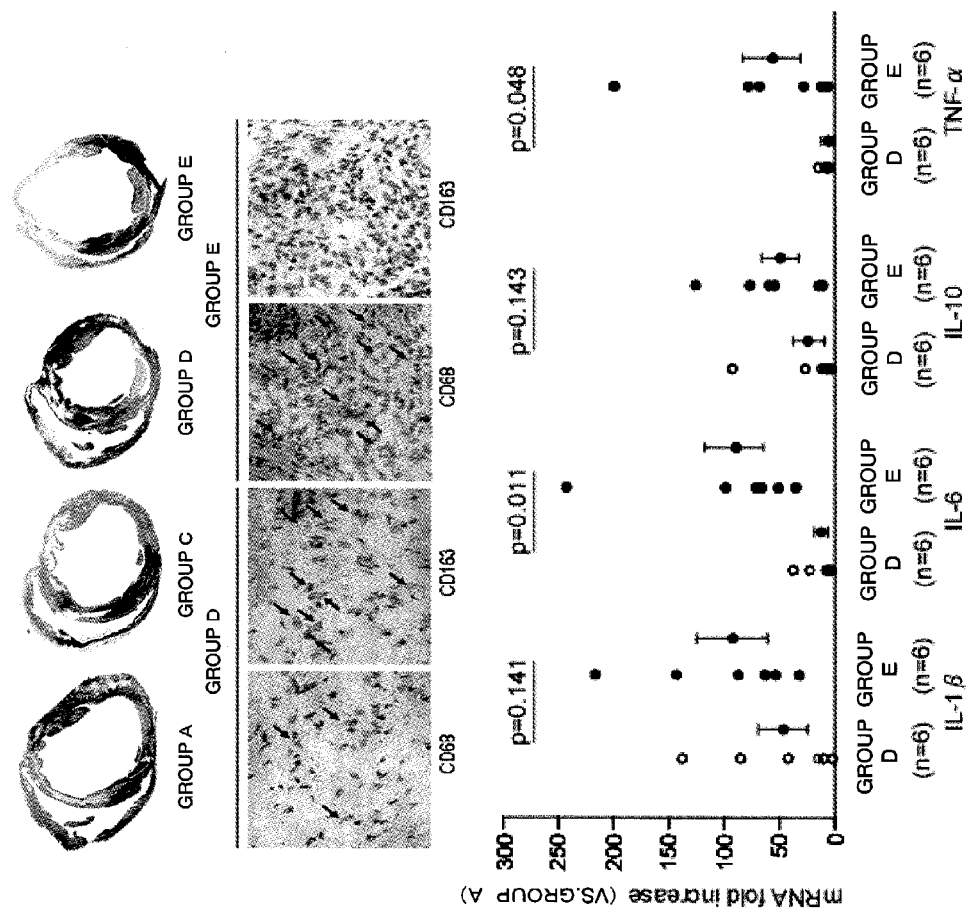
FIG. 13 is a diagram showing the results of analyzing the morphology of myocardial fibrosis and the degree of macrophage invasion in ischemic hearts. In the diagram, the upper photographs respectively show the results of Masson-trichrome-staining the cardiac muscles of miniature pig hearts in each group. The lower photographs respectively show the results of staining macrophages CD68 and CD163 present in cardiac muscles in groups D and E.
FIG. 14 is a diagram showing the results of measuring the expression levels of various inflammatory cytokines (IL-1β, IL-6, IL-10, and TNF-α) in the cardiac muscles of miniature pig hearts in groups D and E 28 days after transplantation therapy.

28 days after transplantation therapy, the miniature pigs in each group were analyzed for the morphology of myocardial fibrosis and the degree of macrophage invasion in the cardiac muscles of their hearts. The cardiac muscles of the hearts of the miniature pigs in each group were Masson-trichrome-stained to visualize fibrotic cells. Moreover, macrophages CD68 and CD163 present in the cardiac muscles in the groups D and E were stained. The results are shown in FIG. 13. The upper photographs of FIG. 13 respectively show the results of Masson-trichrome-staining the cardiac muscles of the miniature pig hearts in each group. Moreover, the lower photographs of FIG. 13 respectively show the results of staining macrophages CD68 and CD163 present in the cardiac muscles in the groups D and E. From these results, the strongest myocardial fibrosis was observed in the group E administered with the combination of the bFGF-containing gelatin hydrogel and the pluripotent stem cells (dose: $5\times10^6$ to $6\times10^6$ cells/kg). Moreover, a lower level of the anti-inflammatory macrophage CD163 and a higher level of the inflammation-inducing macrophage CD68 were confirmed in the group D than those in the group E. Specifically, the results of this test also showed that sufficient therapeutic effect on myocardial infarction was observed in the group D administered with the combination of the bFGF-containing gelatin hydrogel and the pluripotent stem cells (dose: $5\times10^5$ to $6\times10^5$ cells/kg), but not given to the group E administered with the combination of the bFGF-containing gelatin hydrogel and the pluripotent stem cells (dose: $5\times10^6$ to $6\times10^6$ cells/kg).

<Analysis of Expression Levels of Inflammatory Cytokines>

28 days after transplantation therapy, the miniature pigs in the groups D and E were measured for the expression levels of various inflammatory cytokines (IL-1β, IL-6, IL-10, and TNF-α) in the cardiac muscles of their hearts. The results are shown in FIG. 14. Significantly higher expression of the inflammatory cytokines IL-6 and TNF-alpha was observed in the group E than that in the group D.

<Conclusion>

From these results, much more excellent therapeutic effect on myocardial infarction was observed in the group D administered with the combination of the bFGF-containing gelatin hydrogel and the pluripotent stem cells (dose: $5\times10^5$ to $6\times10^5$ cells/kg) than that in the other groups. The therapeutic effect on myocardial infarction observed in the group D is at a level unfeasible by conventional therapy, and the clinical practice thereof is strongly demanded.

Moreover, effective therapeutic effect on myocardial infarction was not observed in the group E administered with the combination of the bFGF-containing gelatin hydrogel and the pluripotent stem cells (dose: $5\times10^6$ to $6\times10^6$ cells/kg). This demonstrated that setting of the dose of the pluripotent stem cells to 10×10$^5$ cells/kg or less in their combined use with the bFGF-containing gelatin hydrogel is of critical significance in achieving improvement in the survival of the grafted pluripotent stem cells and clinically effective cardiomyocyte regeneration.

In this context, the miniature pigs are experimental animals suitable as human models. It is well known in the art that the effective dose of a drug demonstrated from animal tests using the miniature pigs as models is also applicable to the dose of the drug to humans. Thus, these test results sufficiently support therapeutic effectiveness observed in the combined administration of the bFGF-containing gelatin hydrogel and the pluripotent stem cells (dose: 1×10$^5$ to 10×10$^5$ cells/kg, preferably 3×10$^5$ to 8×10$^5$ cells, more preferably 5×10$^5$ to 7×10$^5$ cells) to humans.

Example 4

Proliferative Effect of bFGF on Various Cells

Figure 15:
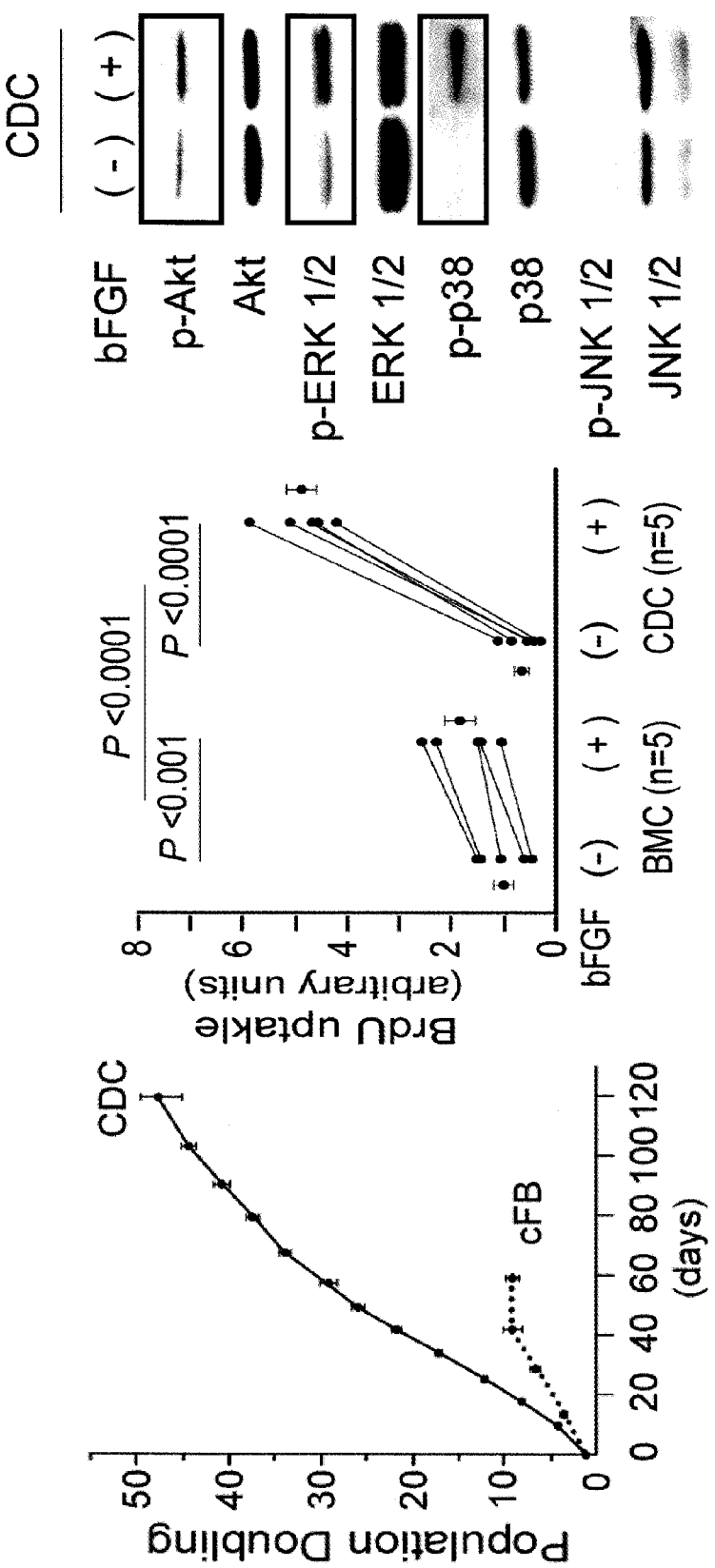
FIG. 15 is a diagram showing growth curves during culture of human cardiac stem cells (CDC: cardiosphere-derived cell) and human fibroblasts (cFB) purified from the same sample thereas (ordinate: population doubling level, abscissa: the number of days; left graph), the ability to synthesize DNA (BrdU uptake, BMC: bone marrow stem cell used as a control group; middle graph), and the phosphorylation of each tyrosine kinase 10 minutes after bFGF stimulation (right graph)

According to Example 2, human heart tissue-derived pluripotent stem cells were prepared. The proliferative effect of bFGF was compared between the heart tissue-derived pluripotent stem cells (CDC) and fibroblasts (cFB) purified from the same sample thereas. As shown in FIG. 15 (left graph), the proliferative effect of bFGF was significant only on the heart tissue-derived pluripotent stem cells and did not proliferate so many fibroblasts (cFB) purified from the same sample thereas.

Moreover, the proliferative effect of bFGF was compared as the ability to synthesize DNA between the heart tissue-derived pluripotent stem cells (CDC) and bone marrow stem cells (BMC) purified from the same sample thereas. The ability to synthesize DNA was evaluated based on BrdU uptake, and values before and after bFGF stimulation and the absolute value of the rate of change in uptake ability in each group were statistically studied. As shown in FIG. 15 (middle graph), the proliferative effect of bFGF was significant only on the heart tissue-derived pluripotent stem cells and did not proliferate so many bone marrow stem cells (BMC) purified from the same sample thereas.

Furthermore, the phosphorylation of each tyrosine kinase 10 minutes after the bFGF stimulation of the human heart tissue-derived pluripotent stem cells was studied by western blotting. As shown in FIG. 15 (right graph), the evident phosphorylation of Akt, ERK1/2, and p38 was observed in the cells stimulated with bFGF, demonstrating that the bFGF proliferates the cells through the signal transduction system mediated by these proteins.

Subsequently, other growth factors (HGF and IGF-1) were studied for their proliferative effect on the human heart tissue-derived pluripotent stem cells. As a result, the addition of HGF or IGF-1 did not proliferate the cells at a level detectable by visual observation (data not shown).

Example 5

Confirmation of Safety (Presence or Absence of Complication of Teratoma)

According to Example 3, miniature pigs with myocardial infarction were prepared. 1 month after the onset of chronic myocardial infarction, the bFGF-containing gelatin hydrogel and the human heart tissue-derived pluripotent stem cells (CDC) were cotransplanted to the miniature pigs, and this treated group (bFGF+CDC) was compared with an untreated group (control). FIGS. 16A and 16B show time-dependent change (before transplantation, 4 weeks after transplantation, 16 weeks after transplantation) in left ventricular ejection fraction (LVEF; FIG. 16A) or infarction size (infarct volume; FIG. 16B). Furthermore, the survival of grafted donor cells (CDC) in both the groups was evaluated by MRI after cell transplantation. FIG. 16C shows a typical MRI image on the 16th week (the yellow arrow represents successfully grafted donor cells), and FIG. 16D shows the results of evaluating over time the survival of grafted donor cells in the bFGF+CDC-transplanted group, with the survival rate of the graft on the 4th day (corresponding to immediately after transplantation) as 100%.

Figure 16:
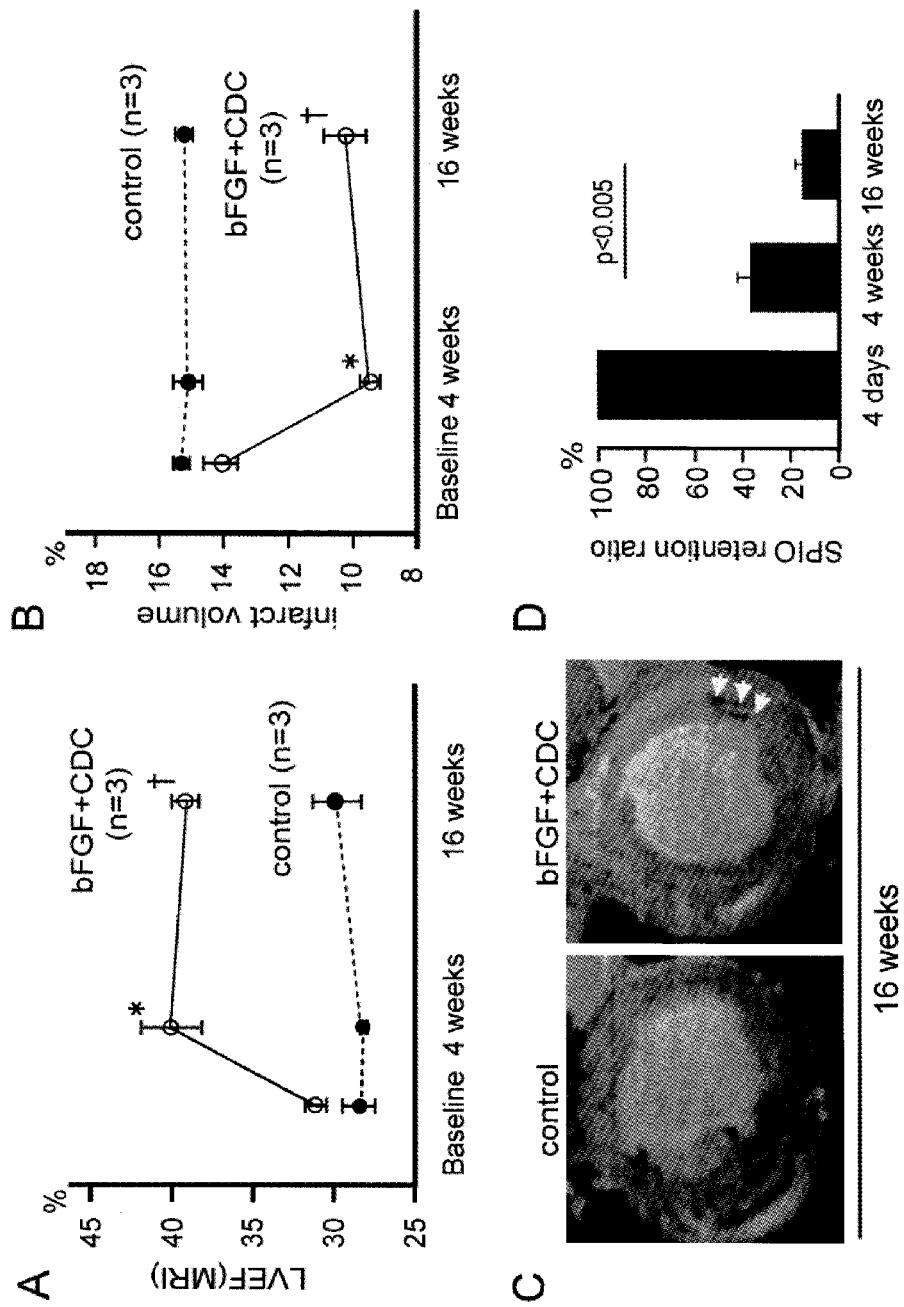
FIGS. 16A and 16B are respectively a diagram showing time-dependent change in left ventricular ejection fraction (LVEF.
FIG. 16C is a diagram showing the survival of grafted donor cells (CDC) (the arrow represents successfully grafted donor cells) in both the groups.
FIG. 16D is a diagram showing the results of evaluating over time the survival of grafted donor cells in the bFGF+CDC-transplanted group.

As shown in FIG. 16, the effect of the cotransplantation of the bFGF-containing gelatin hydrogel and the human heart tissue-derived pluripotent stem cells (CDC) according to the present invention was maintained over the long term, and no complication of teratoma was observed.

All publications, patents, and patent applications cited herein are incorporated herein by reference in their entirety.
Industrial Applicability A preparation for treating heart disease of the present invention can markedly improve the survival of grafted pluripotent stem cells derived from heart tissue and can regenerate cardiomyocytes in the treatment of heart disease using cell therapy. Using the preparation of the present invention, cell therapy for heart disease can achieve the degree of amelioration of the disease unfeasible by conventional cell therapy. Thus, the present invention is useful as a preparation for treating heart disease in patients in need of heart transplantation, terminal heart failure patients having the difficulty in living without the aid of artificial heart, or patients equivalent thereto.

The invention claimed is:

1. A preparation for treating heart disease used in cell therapy, comprising: a hydrogel in a sheet form containing a basic fibroblast growth factor; and
    pluripotent stem cells derived from human heart tissue, wherein the preparation is formulated such that the basic fibroblast growth factor is administered in an amount of at least 1 to 100 µg with respect to the amount of the pluripotent stem cells of 1×10$^6$ cells.

2. The preparation according to claim 1, wherein the preparation is formulated as a kit comprising the hydrogel and the pluripotent stem cells.

3. The preparation according to claim 1, wherein the hydrogel is at least one hydrogel selected from the group consisting of gelatin, collagen, starch, pectin, hyaluronic acid, chitin, chitosan, and alginic acid, and derivatives of these materials.

4. The preparation according to claim 3, wherein the hydrogel is a collagen or gelatin hydrogel.

5. The preparation according to claim 1, wherein the preparation is formulated such that the dose of the hydrogel containing a basic fibroblast growth factor is 1 to 100 µg per kg body weight of a patient in terms of the amount of the basic fibroblast growth factor.

6. The preparation according to claim 1, further comprising a non-biodegradable polymer support.

7. The preparation according to claim 6, wherein the hydrogel is immobilized on the non-biodegradable polymer support when the preparation is administered.

8. The preparation according to claim 7, wherein the non-biodegradable polymer support is polytetrafluoroethylene.

9. The preparation according to claim 1, wherein the preparation is formulated such that the pluripotent stem cells are administered in an amount of 1×10$^6$ cells or less per kg body weight of a patient.

10. The preparation according to claim 9, wherein the preparation is formulated such that the pluripotent stem cells are administered in an amount of $1\times10^5$ to $10\times10^5$ cells per kg body weight of a patient.

11. The preparation according to any of claim 1, wherein the pluripotent stem cells are CD90-positive, CD29-positive, CD73-positive, stro-1-positive, and CD105-positive.

12. The preparation according to claim 1, wherein the pluripotent stem cells are derived from heart tissue of a patient.

13. The preparation according to claim 1, wherein the pluripotent stem cells are derived from heart tissue other than that of a patient.

14. The preparation according to claim 1, wherein the pluripotent stem cells are an established cell line.

15. A method for treating heart disease, comprising:
    administering to a patient the preparation according to claim 1.

16. The method according to claim 15, wherein the preparation hydrogel is immobilized on a non-biodegradable polymer support.

17. The method according to claim 15, wherein the preparation is formulated such that the pluripotent stem cells are administered in an amount of $1\times10^5$ to $10\times10^5$ cells per kg body weight of a patient.

18. The method according to claim 15, wherein the preparation is formulated such that the pluripotent stem cells are administered in an amount of $1\times10^6$ cells or less per kg body weight of a patient.

19. The preparation according to claim 11, wherein the pluripotent stem cells are c-kit-negative.

* * * * *

UNITED STATES PATENT AND TRADEMARK OFFICE
CERTIFICATE OF CORRECTION

PATENT NO. : 8,414,924 B2  Page 1 of 1
APPLICATION NO. : 12/681940
DATED : April 9, 2013
INVENTOR(S) : Oh et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 336 days.

Signed and Sealed this

First Day of September, 2015

Michelle K. Lee
*Director of the United States Patent and Trademark Office*